(12) United States Patent
Jang et al.

(10) Patent No.: US 11,056,655 B2
(45) Date of Patent: Jul. 6, 2021

(54) ORGANIC COMPOUND FOR OPTOELECTRIC DEVICE AND ORGANIC OPTOELECTRIC DEVICE AND DISPLAY DEVICE

(71) Applicant: SAMSUNG SDI CO., LTD., Yongin-si (KR)

(72) Inventors: Kipo Jang, Suwon-si (KR); Byoungkwan Lee, Suwon-si (KR); Youngkwon Kim, Suwon-si (KR); Eun Sun Yu, Suwon-si (KR); Sung-Hyun Jung, Suwon-si (KR); Ho Kuk Jung, Suwon-si (KR)

(73) Assignee: SAMSUNG SDI CO., LTD., Yongin-si (KR)

(*) Notice: Subject to any disclaimer, the term of this patent is extended or adjusted under 35 U.S.C. 154(b) by 464 days.

(21) Appl. No.: 15/473,991

(22) Filed: Mar. 30, 2017

(65) Prior Publication Data

US 2017/0365795 A1 Dec. 21, 2017

(30) Foreign Application Priority Data

Jun. 17, 2016 (KR) ........................ 10-2016-0076024

(51) Int. Cl.
*H01L 51/54* (2006.01)
*H01L 51/00* (2006.01)
*C07D 487/16* (2006.01)
*C09K 11/02* (2006.01)
*H01L 51/50* (2006.01)
*H01L 51/52* (2006.01)

(52) U.S. Cl.
CPC ........ *H01L 51/0072* (2013.01); *C07D 487/16* (2013.01); *C09K 11/025* (2013.01); *H01L 51/0067* (2013.01); *H01L 51/5016* (2013.01); *H01L 51/5206* (2013.01); *H01L 51/5221* (2013.01); *H01L 2251/5384* (2013.01)

(58) Field of Classification Search
CPC .. C07D 487/00; C07D 487/02; C07D 487/04; C07D 487/10; C07D 487/12; C07D 487/16; C09K 11/025; C09K 11/06; C09K 2211/00; C09K 2211/10; C09K 2211/1007; C09K 2211/1011; C09K 2211/1014; C09K 2211/1018; C09K 2211/1022; C09K 2211/1044; H01L 51/0032; H01L 51/005; H01L 51/0067; H01L 51/0072; H01L 51/50; H01L 51/5012; H01L 51/5016; H01L 51/5221; H01L 51/5206; H01L 2251/5384
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | |
|---|---|---|---|
| 8,932,731 B2 | 1/2015 | Parham et al. | |
| 2014/0319507 A1 | 10/2014 | Yamamoto et al. | |
| 2017/0213984 A1* | 7/2017 | Kim ....................... | C09K 11/06 |

FOREIGN PATENT DOCUMENTS

| | | | |
|---|---|---|---|
| CN | 106661037 A | 5/2017 | |
| KR | 10-2014-0034710 A | 3/2014 | |
| KR | 10-2014-0064612 A | 5/2014 | |
| KR | 10-2016-0119712 A | 10/2016 | |
| KR | 10-2016-0142792 | 12/2016 | |
| KR | 10-2017-0126814 A | 11/2017 | |
| WO | WO-2016195441 A1 * | 12/2016 | ............. C09K 11/06 |

OTHER PUBLICATIONS

Machine translation of KR2014-0034710. (Year: 2014).*
Chinese Office Action dated Jan. 3, 2019.

* cited by examiner

*Primary Examiner* — Andrew K Bohaty
(74) *Attorney, Agent, or Firm* — Lee IP Law, P.C.

(57) ABSTRACT

Disclosed are a compound for an organic optoelectric device represented by Chemical Formula 1, an organic optoelectric device including the same, and a display device. Details of Chemical Formula 1 are the same as defined in the specification.

15 Claims, 1 Drawing Sheet

【FIG. 1】
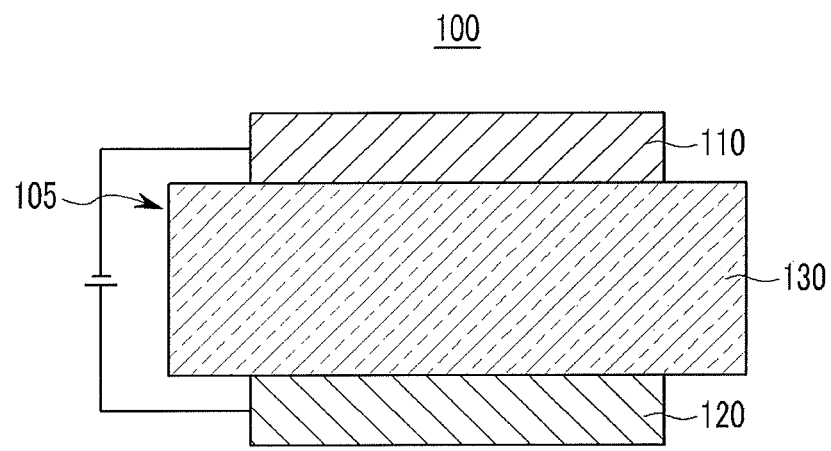
【FIG. 2】
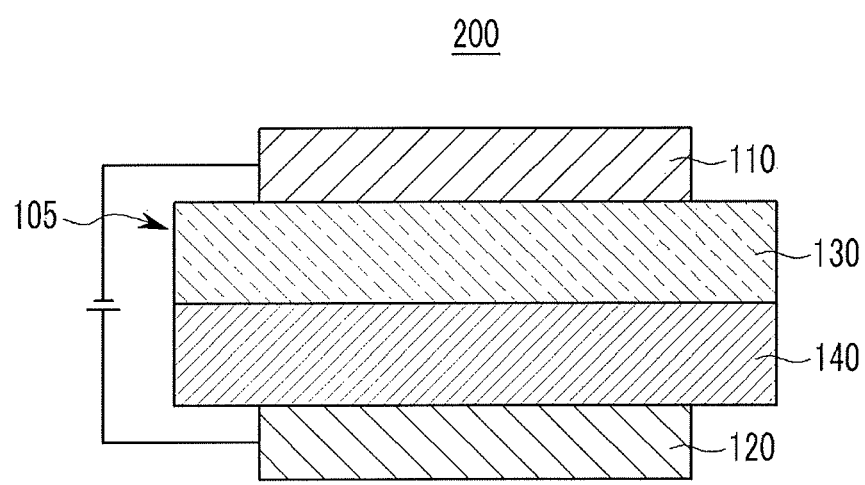

ORGANIC COMPOUND FOR OPTOELECTRIC DEVICE AND ORGANIC OPTOELECTRIC DEVICE AND DISPLAY DEVICE

CROSS-REFERENCE TO RELATED APPLICATION

This application claims priority to and the benefit of Korean Patent Application No. 10-2016-0076024 filed in the Korean Intellectual Property Office on Jun. 17, 2016, the entire contents of which are incorporated herein by reference.

BACKGROUND OF THE INVENTION (a) Field of the Invention

A compound for an organic optoelectric device, an organic optoelectric device, and a display device disclosed.

(b) Description of the Related Art

An organic optoelectric device is a device that converts electrical energy into photoenergy, and vice versa.

An organic optoelectric device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectric device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include an light-emitting layer and optionally an auxiliary layer, and the auxiliary layer may be, for example at least one selected from a hole injection layer, a hole transport layer, an electron blocking layer, an electron transport layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides a compound for an organic optoelectric device capable of realizing an organic optoelectric device having high efficiency and a long life-span.

Another embodiment provides an organic optoelectric device including the compound for an organic optoelectric device.

Yet another embodiment provides a display device including the organic optoelectric device.

According to an embodiment, a compound for an organic optoelectric device represented by Chemical Formula 1 is provided.

[Chemical Formula 1]

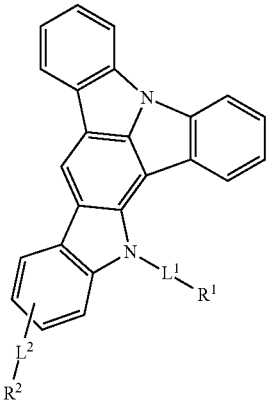

In Chemical Formula 1, $R^1$ and $R^2$ are independently hydrogen, deuterium, a substituted or unsubstituted C6 to C30 aryl group, a substituted or unsubstituted C2 to C30 heterocyclic group, or a combination thereof, at least one of $R^1$ and $R^2$ is an N-containing substituted or unsubstituted C2 to C30 heterocyclic group, $L^1$ and $L^2$ are independently a single bond, a substituted or unsubstituted C6 to C30 arylene group, or a substituted or unsubstituted C2 to C30 heteroarylene group, and the "substituted" refers to replacement of at least one hydrogen by deuterium, a C1 to C30 alkyl group, a C6 to C30 aryl group, or a C2 to C30 heteroaryl group.

According to another embodiment, an organic optoelectric device includes an anode and a cathode facing each other and at least one organic layer disposed between the anode and the cathode, wherein the organic layer includes the compound for an organic optoelectric device.

According to another embodiment, a display device including the organic optoelectric device is provided.

An organic optoelectric device having high efficiency and a long life-span may be realized.

BRIEF DESCRIPTION OF THE DRAWINGS

FIGS. 1 and 2 are cross-sectional views showing organic light emitting diodes according embodiments.

DETAILED DESCRIPTION

Hereinafter, embodiments of the present invention are described in detail. However, these embodiments are exemplary, the present invention is not limited thereto and the present invention is defined by the scope of claims.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C6 to C30 heteroaryl group, a C1 to C20 alkoxy group, a C1 to C10 trifluoroalkyl group, a cyano group, or a combination thereof.

As used herein, when a definition is not otherwise provided, "hetero" refers to one including one to three heteroatoms selected from N, O, S, P, and Si, and remaining carbons in one functional group.

As used herein, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

An aryl group may include a monocyclic, polycyclic or fused ring polycyclic (i.e., rings sharing adjacent pairs of carbon atoms) functional group.

As used herein, "heterocyclic group" is a generic concept of a heteroaryl group, and may include at least one hetero atom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted phenanthrolinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, a substituted or unsubstituted benzoquinazolinyl group, or a combination thereof, but are not limited thereto.

In the present specification, a single bond refers to a direct bond not by carbon or a hetero atom except carbon, and specifically the meaning that L is a single bond means that a substituent linked to L directly bonds with a central core. That is, in the present specification, the single bond does not refer to methylene that is bonded via carbon.

In the present specification, hole characteristics refer to an ability to donate an electron to form a hole when an electric field is applied, and that a hole formed in the anode may be easily injected into a light-emitting layer, and a hole formed in a light-emitting layer may be easily transported into an anode and transported in the light-emitting layer due to conductive characteristics according to a highest occupied molecular orbital (HOMO) level.

In addition, electron characteristics refer to an ability to accept an electron when an electric field is applied, and that an electron formed in a cathode may be easily injected into a light-emitting layer, and an electron formed in a light-emitting layer may be easily transported into a cathode and transported in the light-emitting layer due to conductive characteristics according to a lowest unoccupied molecular orbital (LUMO) level.

Hereinafter, a compound for an organic optoelectric device according to an embodiment is described.

A compound for an organic optoelectric device according to an embodiment is represented by Chemical Formula 1.

[Chemical Formula 1]

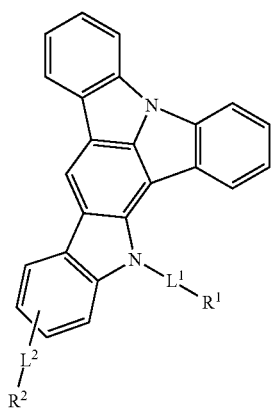

In Chemical Formula 1, $R^1$ and $R^2$ are independently hydrogen, deuterium, a substituted or unsubstituted C6 to C30 aryl group, a substituted or unsubstituted C2 to C30 heterocyclic group, or a combination thereof, at least one of $R^1$ and $R^2$ is an N-containing substituted or unsubstituted C2 to C30 heterocyclic group, $L^1$ and $L^2$ are independently a single bond, a substituted or unsubstituted C6 to C30 arylene group, or a substituted or unsubstituted C2 to C30 heteroarylene group, and the "substituted" refers to replacement of at least one hydrogen by deuterium, a C1 to C30 alkyl group, a C6 to C30 aryl group, or a C2 to C30 heteroaryl group.

In one example of the present invention, "substituted" of "substituted or unsubstituted" refers to replacement of at least one hydrogen by deuterium, a C1 to C4 alkyl group, a C6 to C18 aryl group, or a C2 to C18 heteroaryl group.

In another example of the present invention, "substituted" of "substituted or unsubstituted" refers to replacement of at least one hydrogen by deuterium, a C1 to C4 alkyl group, a phenyl group, a biphenyl group, a naphthyl group, a terphenyl group, or a pyridinyl group, a pyrimidinyl group, a triazinyl group, a dibenzofuranyl group, a dibenzothiophenyl group, a fluorenyl group, a 9-carbazolyl group, or a 9-phenylcarbazolyl group.

In another example of the present invention, "substituted" of "substituted or unsubstituted" refers to replacement of at least one hydrogen by deuterium, a C1 to C4 alkyl group, a phenyl group, a biphenyl group, a naphthyl group, a terphenyl group, or a pyridinyl group, a dibenzofuranyl group, a dibenzothiophenyl group, or a fluorenyl group.

The compound for an organic optoelectric device represented by Chemical Formula 1 may have an asymmetrically three dimensional structure due to fusion of azatriphenylene including a "nitrogen (N)" unit with carbazole.

The compound for an organic optoelectric device represented by Chemical Formula 1 has deeper HOMO energy due to additional fusion of indolocarbazole but planarity of the compound is increased relative to the indolocarbazole and thus the compound has fast hole mobility compared relative to the energy level.

Accordingly, the compound shows particularly sufficient characteristics in a low-doped red light-emitting layer compared with a shallow HOMO ambipolar material and thus excellent characteristics as a light-emitting layer material of a long life-span red device. In addition, the compound for an organic optoelectric device having this structure and represented by Chemical Formula 1 may play a role of an electron injection material, an electron transport material, or a light emitting material depending on characteristics of a substituent, and when used as the light emitting material, an organic optoelectric device fast-operated and having high efficiency and a long life-span may be realized.

The compound for an organic optoelectric device may be for example represented by one of Chemical Formulae 1-I, 1-II, and 1-III according to a position of a substituent having hole characteristics or electron characteristics.

[Chemical Formula 1-I]

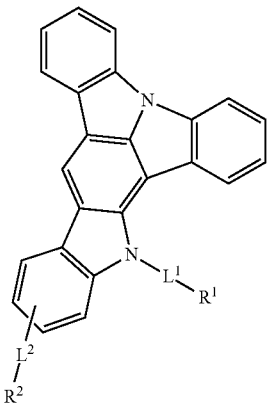

[Chemical Formula 1-II]

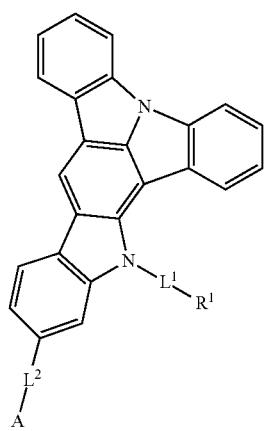

[Chemical Formula 1-III]

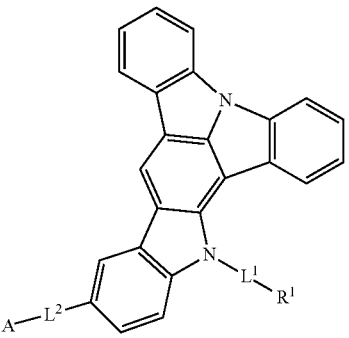

In Chemical Formulae 1-I to 1-III,

A refers to a substituent having hole characteristics or electron characteristics and is an N-containing substituted or unsubstituted C2 to C30 heterocyclic group.

R[1] and R[2] are independently hydrogen, deuterium, a substituted or unsubstituted C6 to C30 aryl group, a substituted or unsubstituted C2 to C30 heterocyclic group, or a combination thereof, and L[1] and L[2] are independently a single bond, a substituted or unsubstituted C6 to C30 arylene group, or a substituted or unsubstituted C2 to C30 heteroarylene group.

In an example embodiment, the N-containing substituted or unsubstituted C2 to C30 heterocyclic group may be a substituted or unsubstituted carbazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted phenanthrolinyl group, a substituted or unsubstituted naphthyridinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted benzoquinazolinyl group, or a combination thereof, and specifically, a substituted or unsubstituted carbazolyl group, a substituted or unsubstituted pyridyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted benzoquinazolinyl group, or a combination thereof, and may be for example selected from substituents of Groups 1-A and 1-B.

[Group 1-A]

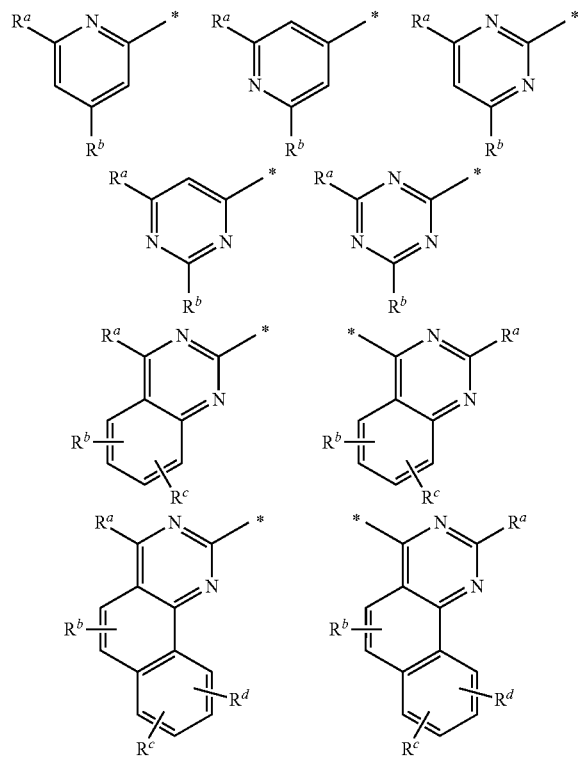

[Group 1-B]

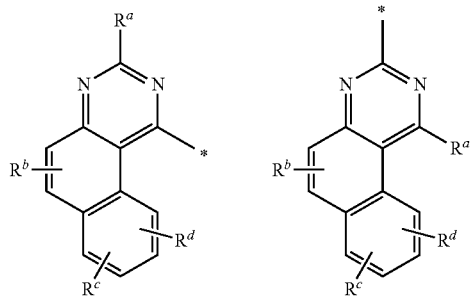

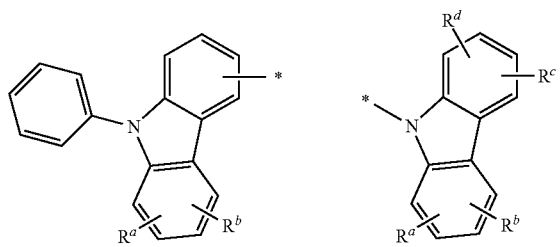

In Groups 1-A and 1-B, $R^a$ to $R^d$ are independently hydrogen, deuterium, a C1 to C30 alkyl group, a C6 to C30 aryl group, or a C2 to C30 heteroaryl group,

* indicates a binding site with an adjacent atom.

When at least one of R[1] and R[2] of Chemical Formula 1 is a substituent having electron characteristics selected from Group 1-A, it may be a material having bipolar characteristics and a balance between a hole and an electron is maintained at a deep HOMO level of a light-emitting layer to realize high efficiency and low driving characteristics. In addition, when it is used with a hole transporting light emitting material, device characteristics of a long life-span and a fast driving voltage may be obtained.

On the other hand, when at least one of R[1] and R[2] of Chemical Formula 1 is a substituent having hole characteristics selected from Group 1-B, a material having very fast hole mobility may be prepared.

In specific example embodiments, at least one of R[1] and R[2] may be selected from substituents of Group 1-A1 or substituents of Group 1-B1.

[Group 1-A1]

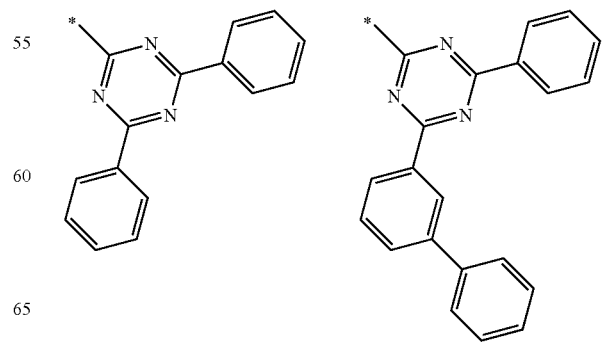

-continued
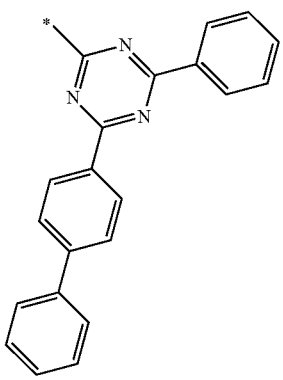
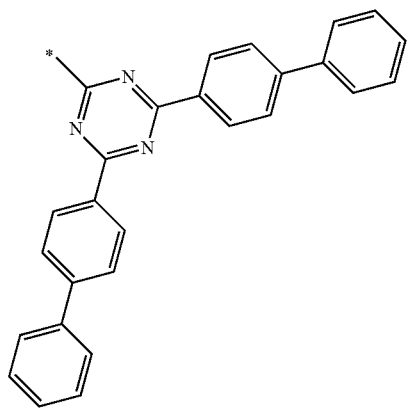
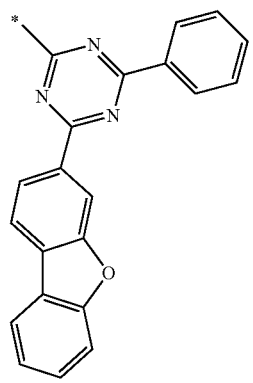
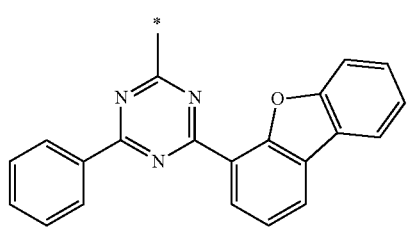
-continued
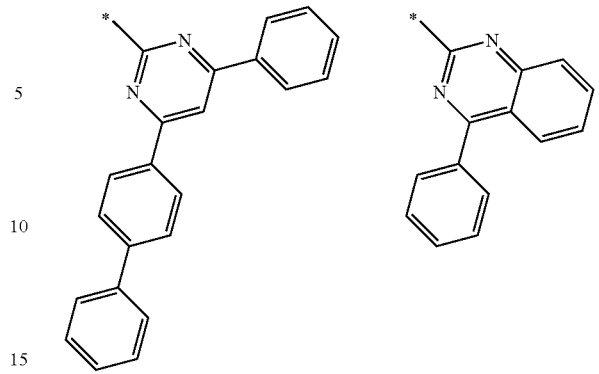
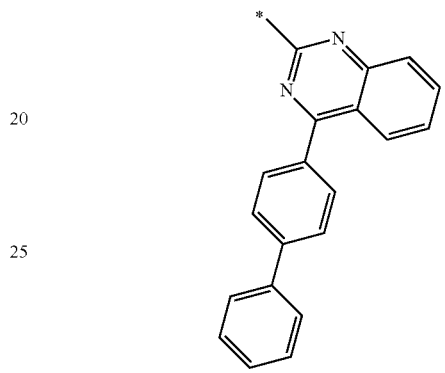
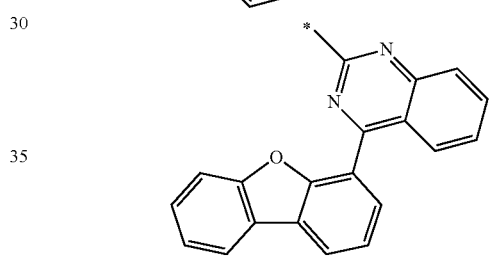
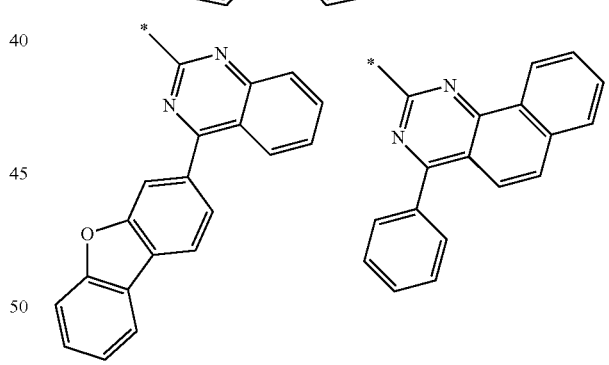
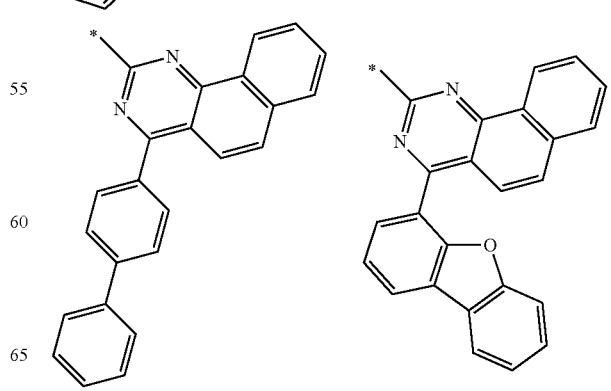

[Group 1-B1]

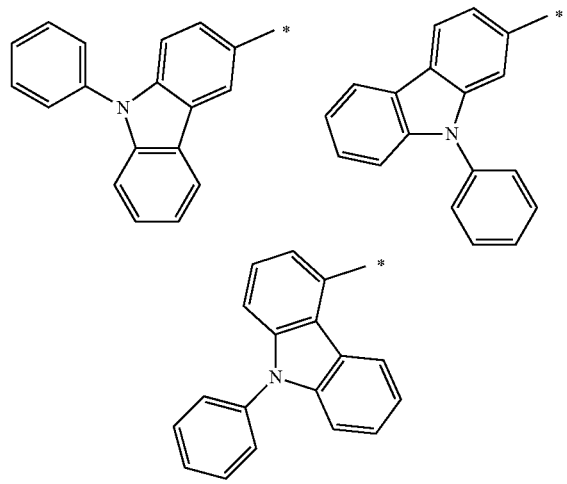

In Groups 1-A1 and 1-B1, * indicates a binding site with an adjacent atom.

In an example embodiment of the present invention, $L^1$ and $L^2$ are independently a single bond, a substituted or unsubstituted phenylene group, a substituted or unsubstituted biphenylene group, or a substituted or unsubstituted terphenylene group, and are specifically a single bond, or selected from a substituted or unsubstituted linking groups of Group 1.

[Group 1]

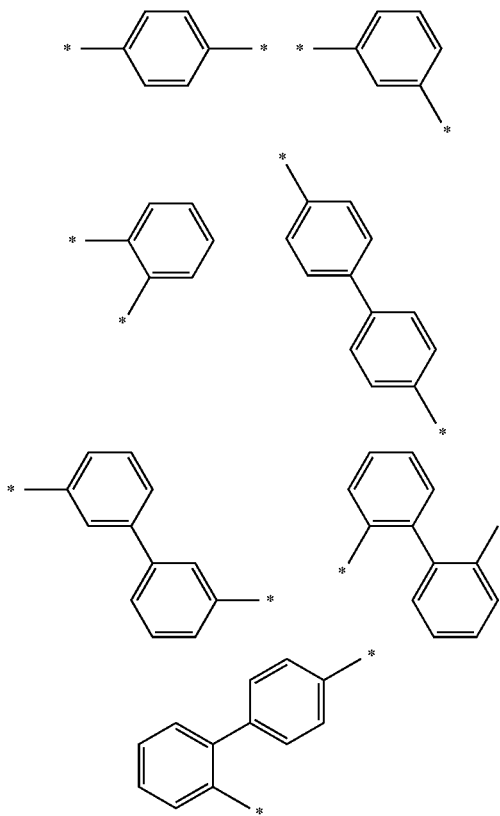

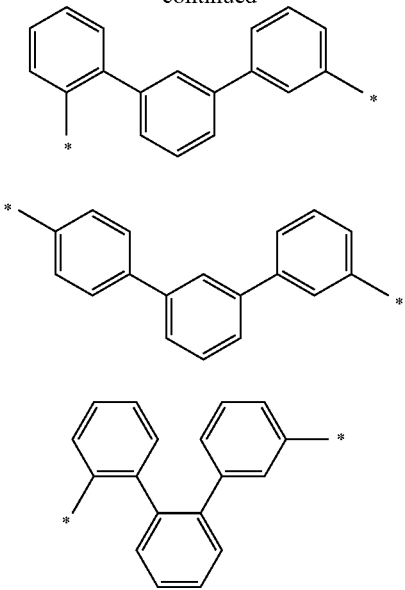

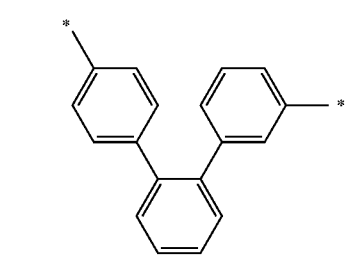

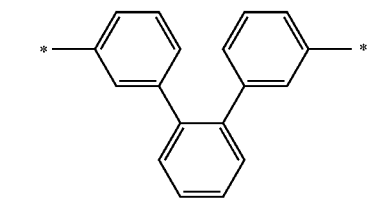

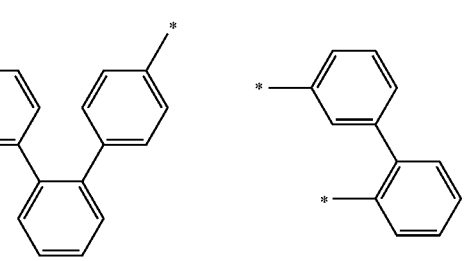

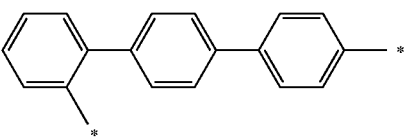

-continued

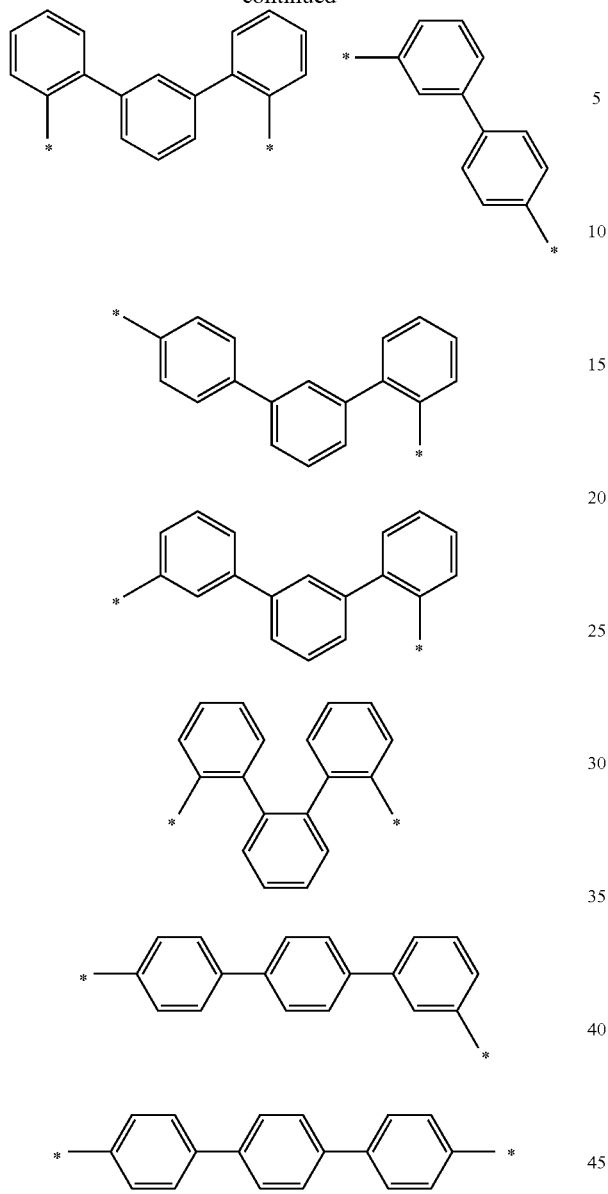

In Group 1, * indicates a binding site with an adjacent atom.

In a more specific example embodiment, $R^1$ and $R^2$ are independently hydrogen, a phenyl group, a substituted or unsubstituted carbazolyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, or a substituted or unsubstituted benzoquinazolinyl group, at least one of $R^1$ and $R^2$ is selected from substituents of Groups 1-A1 and 1-B1, and $L^1$ and $L^2$ are a single bond, a phenylene group, or a biphenylene group. In one example of the present invention, $L^1$ and $L^2$ are a single bond, a phenylene group, or a meta-biphenylene group.

The compound for an organic optoelectric device may be for example selected from compounds of Group 2, but is not limited thereto.

[Group 2]

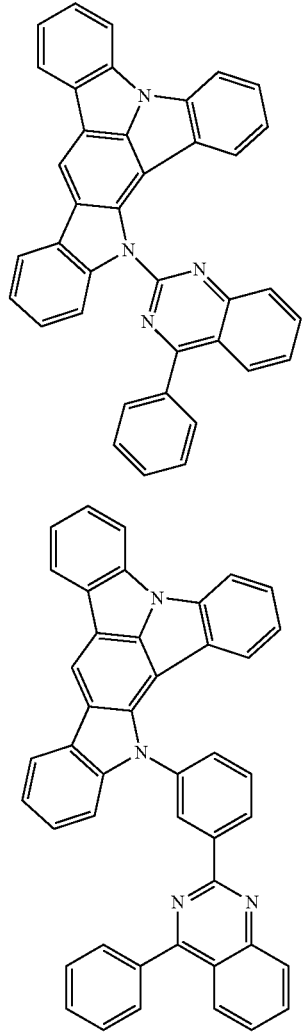

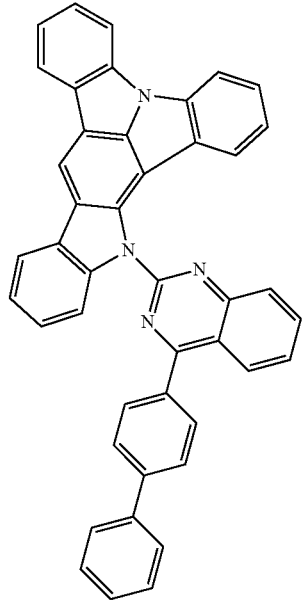

[A-4]
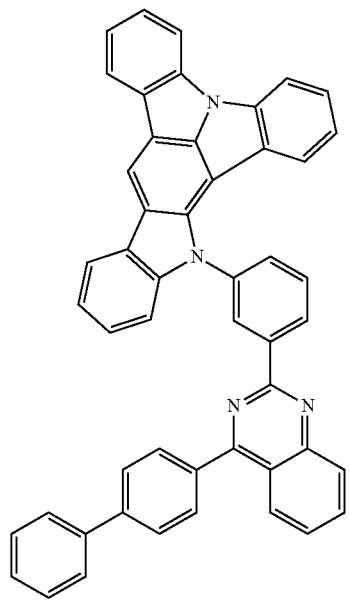
[A-5]
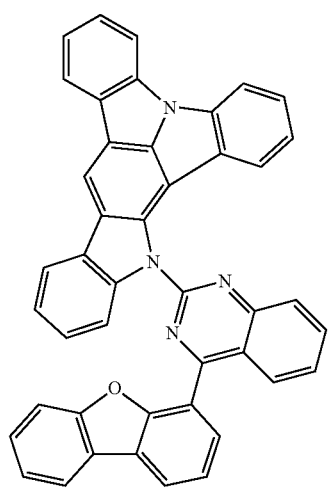
[A-6]
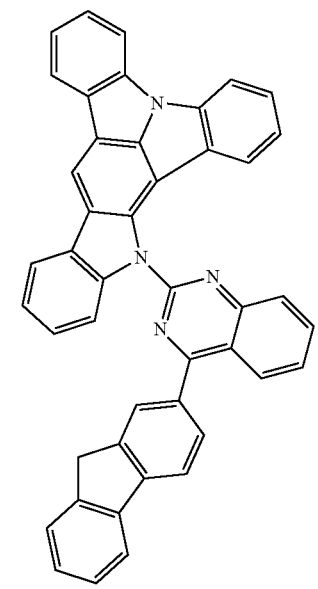
[A-7]
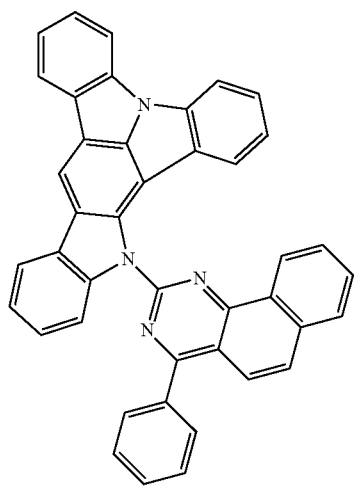
[A-8]
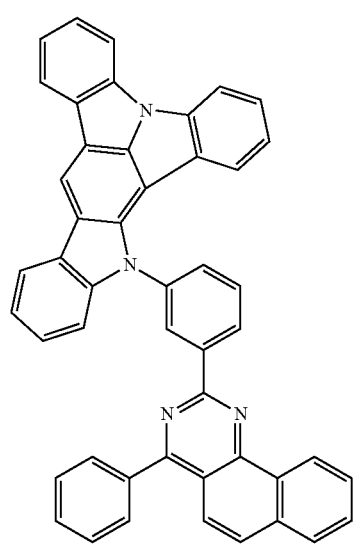
[A-9]
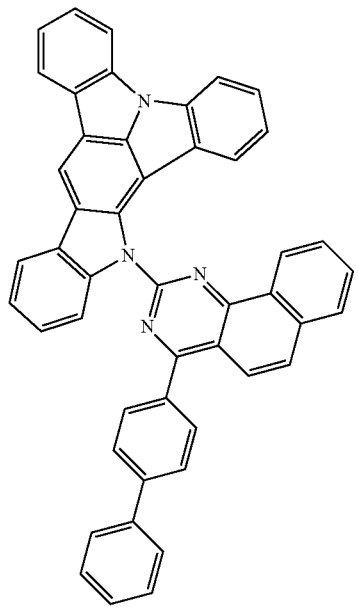

[A-10]
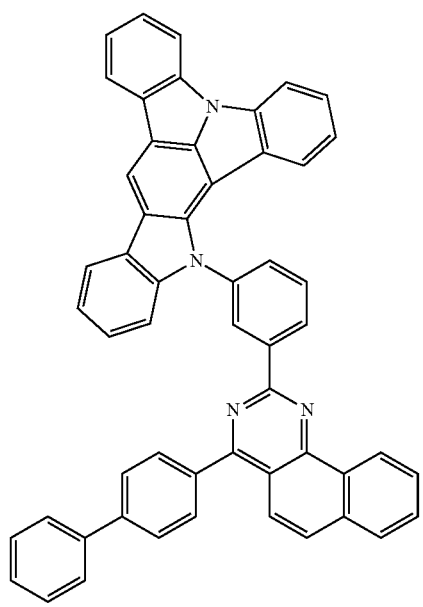
[A-11]
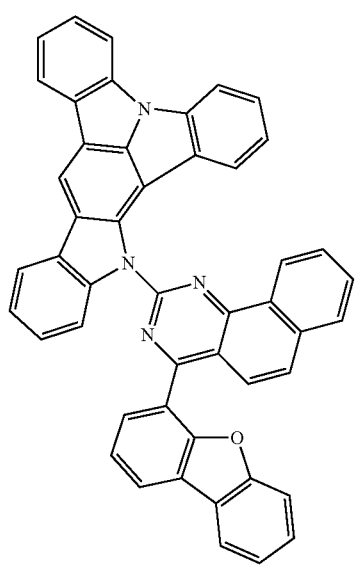
[A-12]
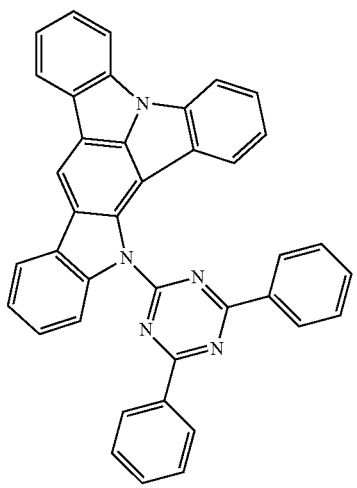
[A-13]
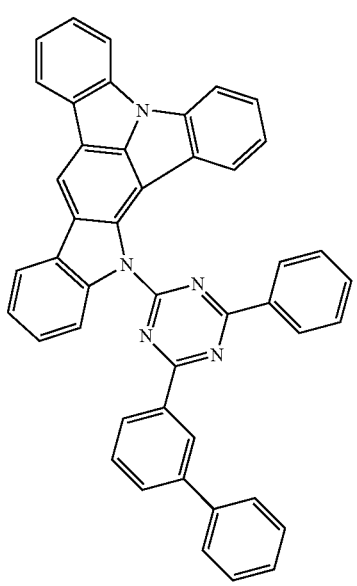
[A-14]
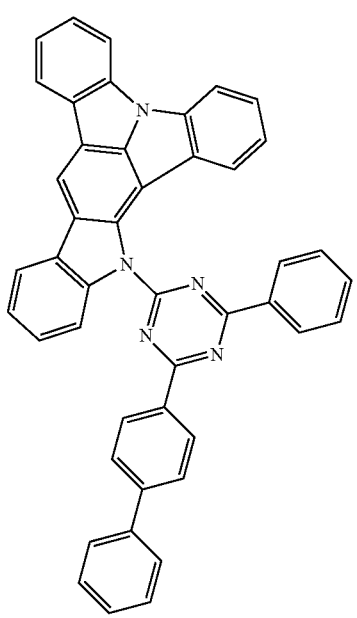

[A-15]
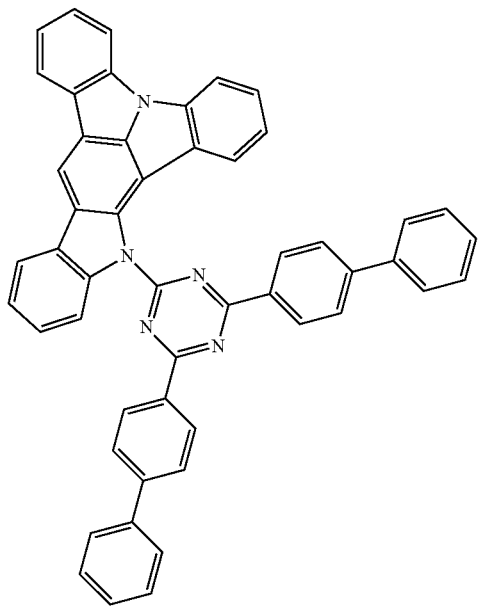
[A-16]
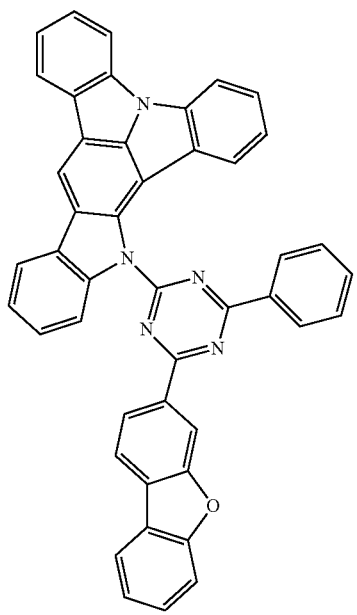
[A-17]
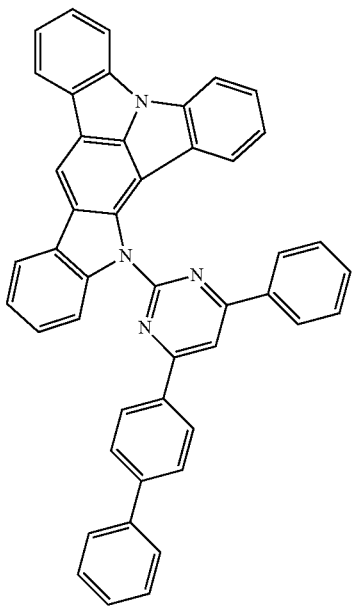
[A-18]
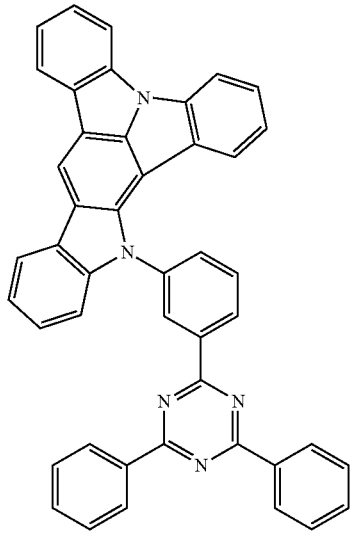

[A-19]
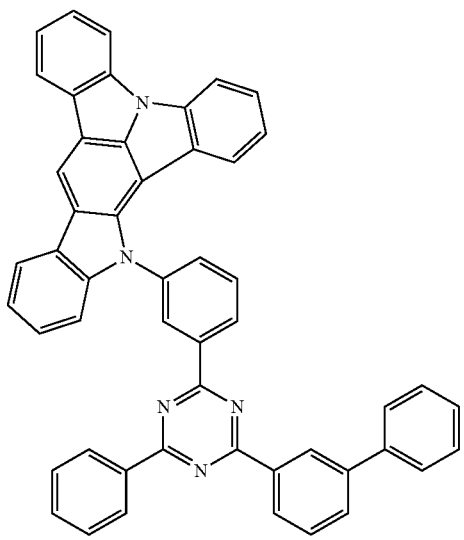
[A-20]
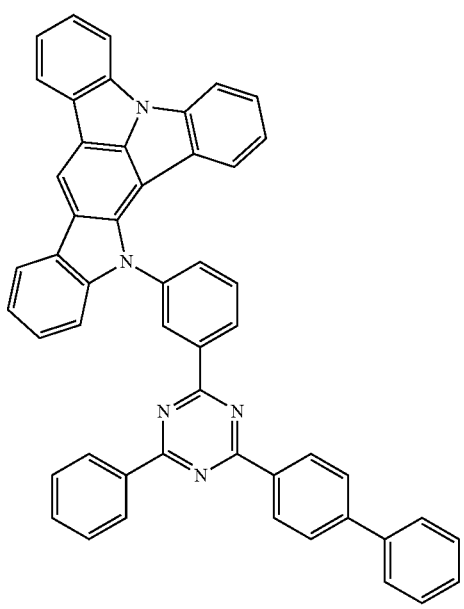
[A-21]
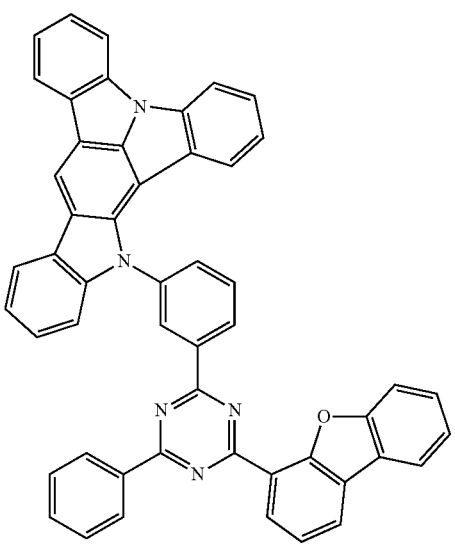
[B-1]
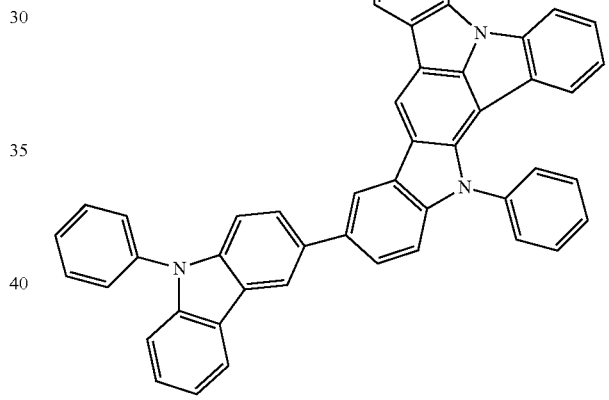
[B-2]

[B-3]
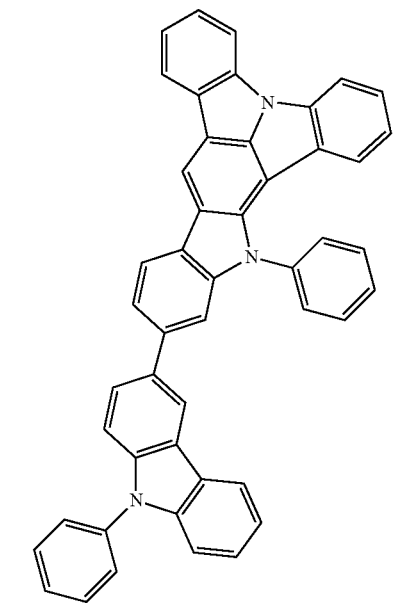
[B-4]
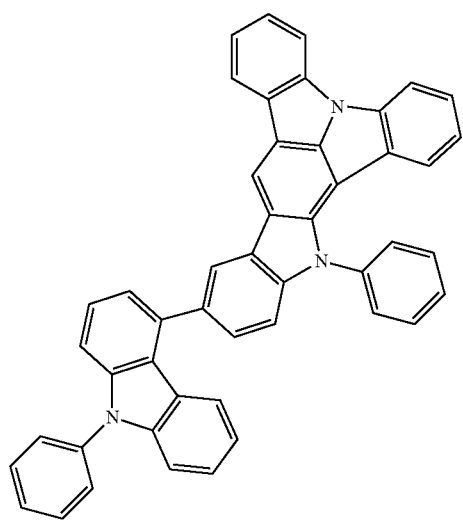
[B-5]
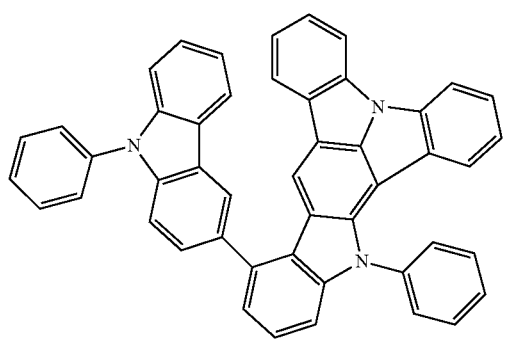
[B-6]
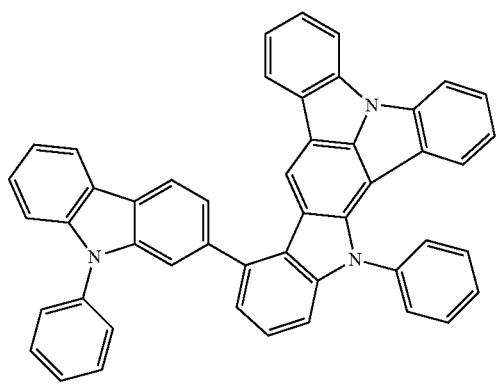
[B-7]
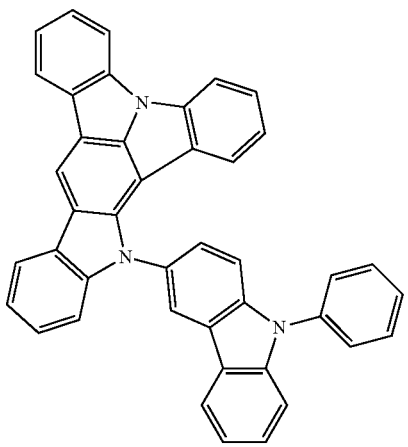
[B-8]
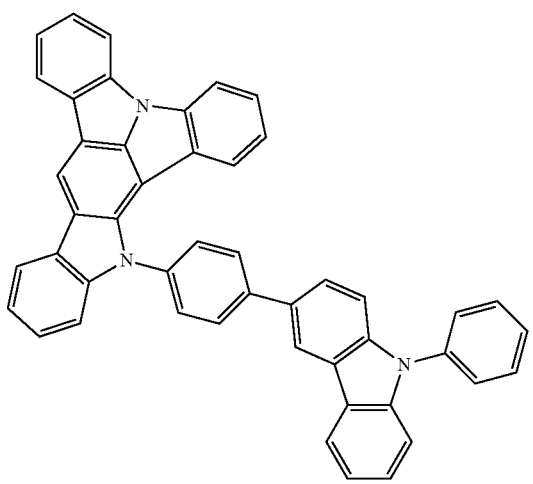

[C-1]
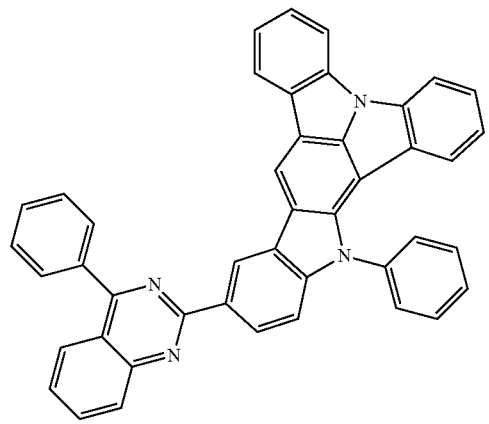
[C-2]
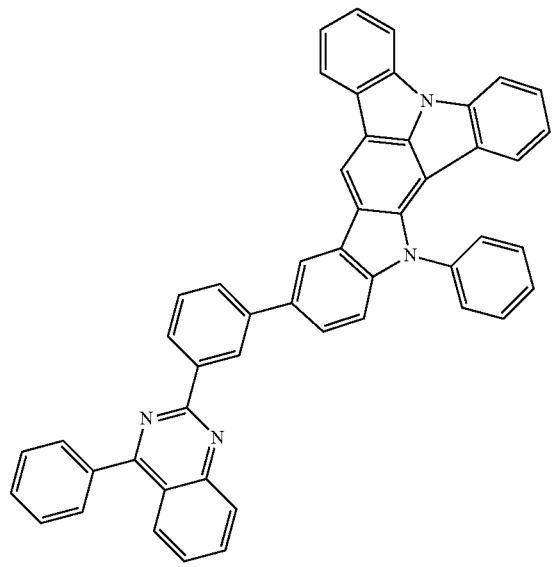
[C-3]
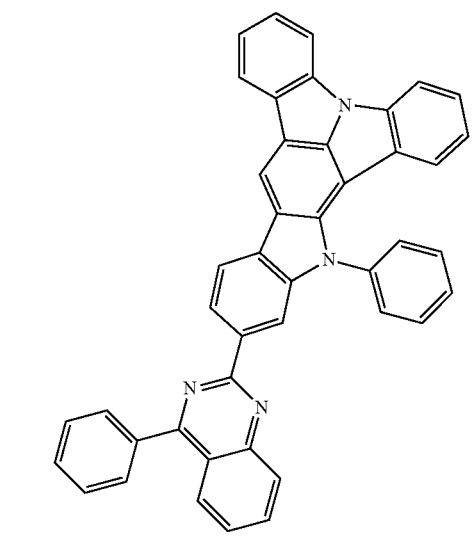
[C-4]
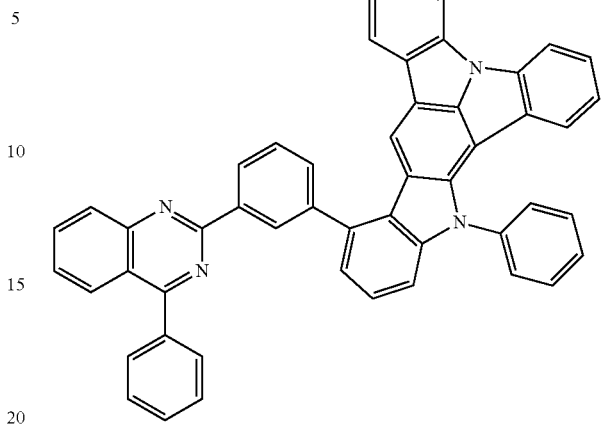
[C-5]
[C-6]
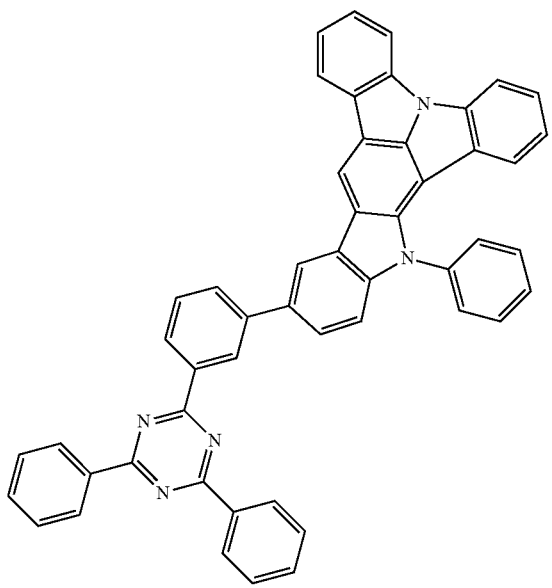

-continued

[C-7]

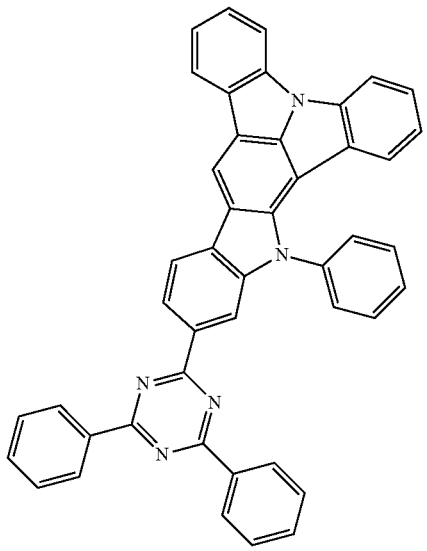

[C-8]

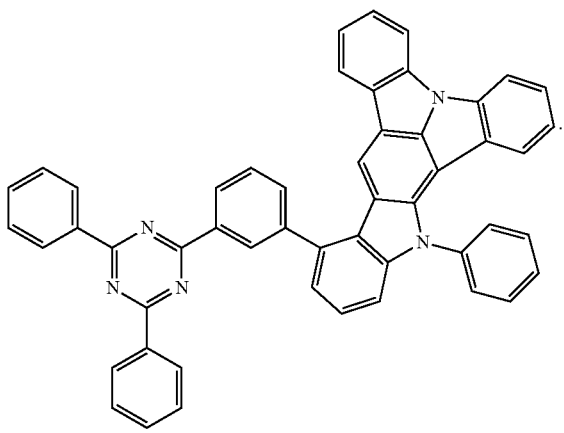

Hereinafter, an organic optoelectric device including the compound for an organic optoelectric device is described.

The organic optoelectric device may be any device to convert electrical energy into photoenergy and vice versa without particular limitation, and may be, for example an organic photoelectric device, an organic light emitting diode, an organic solar cell, and an organic photo conductor drum.

The organic optoelectric device may include an anode and a cathode facing each other, and at least one organic layer between the anode and the cathode, wherein the organic layer includes the compound for an organic optoelectric device.

Herein, an organic light emitting diode as one example of an organic optoelectric device is described referring to drawings.

FIGS. 1 and 2 are cross-sectional views showing organic light emitting diodes according to embodiments.

Referring to FIG. 1, an organic light emitting diode 100 according to an embodiment includes an anode 120 and a cathode 110 facing each other and an organic layer 105 between the anode 120 and the cathode 110.

The anode 120 may be made of a conductor having a large work function to help hole injection, and may be for example a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes a light-emitting layer 130 including the compound for an organic optoelectric device.

The light-emitting layer 130 may include, for example the compound for an organic optoelectric device alone, or the composition comprising at least two of the compound for an organic optoelectric device.

The compound for an organic optoelectric device according to an embodiment may be, for example included as a host of a light-emitting layer and may be, for example included as a red host or a green host.

Referring to FIG. 2, an organic light emitting diode 200 further includes a hole auxiliary layer 140 in addition to the light-emitting layer 130. The hole auxiliary layer 140 may further increase hole injection and/or hole mobility and block electrons between the anode 120 and the light-emitting layer 130. The hole auxiliary layer 140 may be, for example a hole transport layer, a hole injection layer, and/or an electron blocking layer, and may include at least one layer. The compound for an organic optoelectric device may be included in the light-emitting layer 130.

In an embodiment of the present invention, in FIG. 1 or 2, an organic light emitting diode may further an electron transport layer, an electron injection layer, a hole injection layer, and the like as an organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

Hereinafter, the embodiments are illustrated in more detail with reference to examples. These examples, however, are not in any sense to be interpreted as limiting the scope of the invention (Synthesis of Compound for Organic Optoelectric Device)

Hereinafter, starting materials and reactants used in Examples and Synthesis Examples were purchased from Sigma-Aldrich Co. Ltd. or TCI Inc. as far as there in no particular comment.

Synthesis Example 1: Synthesis of Compound A-1

[Reaction Scheme 1]

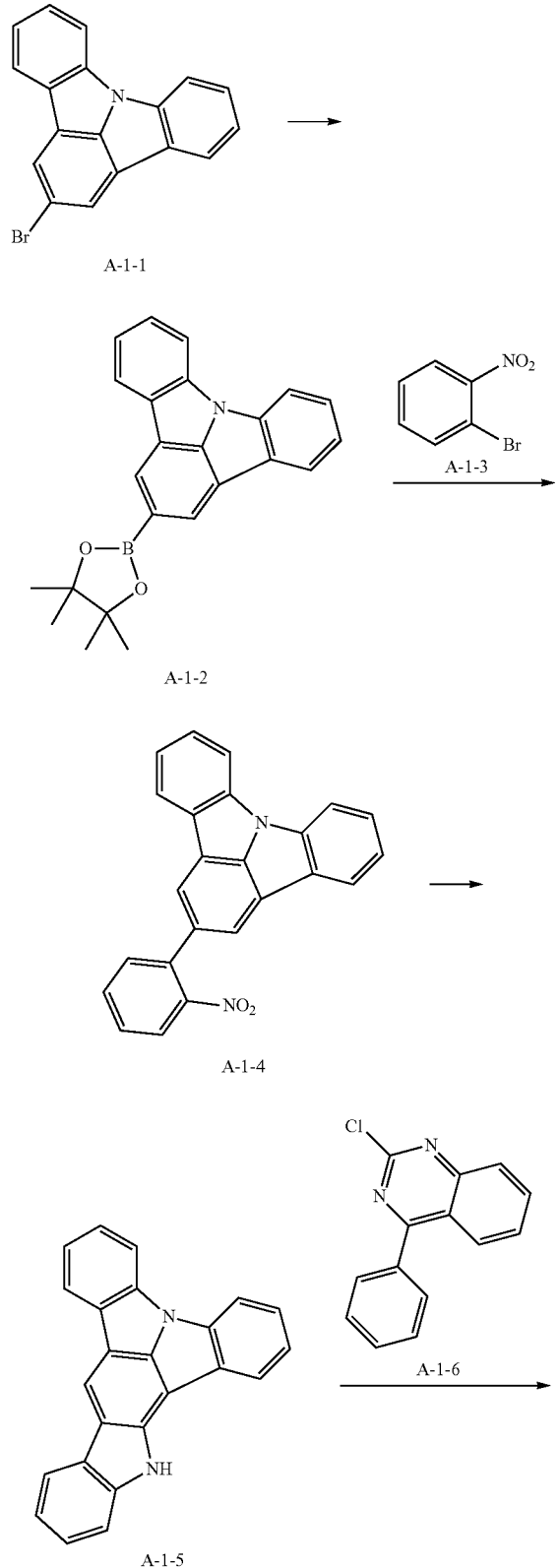

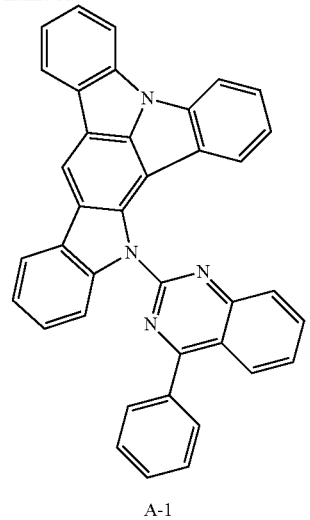

a) Synthesis of Intermediate A-1-2

Intermediate A-1-1 (32.0 g (100 mmol), refer to Synthesis Method A: European Journal, 15 22, 5482-5490, S5482/1-S5482/18; 2009) was added to DMF (250 mL, dimethyl formamide) in a 500 mL round-bottomed flask, 0.05 equivalent of dichlorodiphenylphosphinoferrocene palladium, 1.2 equivalent of bispinacolato diboron, and 2 equivalent of potassium acetate were added thereto, and the mixture was heated and refluxed under a nitrogen atmosphere for 18 hours. The reaction solution was cooled down and added in a dropwise fashion to 1 L of water to obtain a solid. The solid was dissolved in boiling toluene to treat activated carbon and filtered in silica gel, and the filtered solution was concentrated. The concentrated solid was stirred with a small amount of hexane and filtered to obtain Intermediate A-1-2 (31.2 g, 85% of a yield).

b) Synthesis of Intermediate A-1-4

One equivalent of Intermediate A-1-2 (32.2 g (85 mmol)) and 1.2 equivalent of 2-bromonitrobenzene (A-1-3) were added to tetrahydrofuran (200 mL) distilled water (100 mL) in a 500 mL round-bottomed flask, 0.03 equivalent of tetrakistriphenylphosphine palladium and 2 equivalent of potassium carbonate were added thereto, and the mixture was heated and refluxed under a nitrogen atmosphere. After 18 hours, the reaction solution was cooled down, an organic layer was reduced into a half under a reduced pressure after removing an aqueous layer, MeOH (300 mL) was added thereto, and the mixture was stirred. A solid precipitated therein was filtered and washed with water (500 mL). The solid was recrystallized with toluene (200 mL) to obtain Intermediate A-1-4 (21.7 g, 70%=a yield).

c) Synthesis of Intermediate A-1-5

Intermediate A-1-4 (21.7 g (60 mmol)) and 5 equivalent of triethylphosphite were put in a 500 mL round-bottomed flask and stirred at 160° C. for 4 hours. After the reaction, the triethylphosphite was vacuum-purified, methanol (150 mL) was added thereto, and the mixture was stirred. A solid precipitated therein was filtered and washed with water (300 mL). The solid was recrystallized with monochlorobenzene (200 mL) to obtain Intermediate A-1-5 (13.9 g, 70%=a yield).

d) Synthesis of Compound A-1

Intermediate A-1-5 (13.9 g), 1.1 equivalent of 2-chloro-4-phenyl-quinazoline (cas: 29874-83-7), 2 equivalent of sodium t-butoxide, and 0.05 equivalent of $Pd_2(dba)_3$ were suspended in xylene (200 ml), 0.15 equivalent of tri-tertiarybutylphosphine was added thereto, and the mixture was refluxed and stirred for 18 hours. When the reaction was complete, methanol (300 mL) was added thereto, the mixture was stirred, and a solid therein was filtered and washed with water (300 mL). The solid was recrystallized with monochlorobenzene (200 mL) to obtain Compound A-1 (16.8 g, 75%=a yield).

LC/MS calculated for: C38H22N4 Exact Mass: 534.1844 found for 535.19 [M+H].

Synthesis Example 2: Synthesis of Compound A-2

Synthesis Example 3: Compound A-3

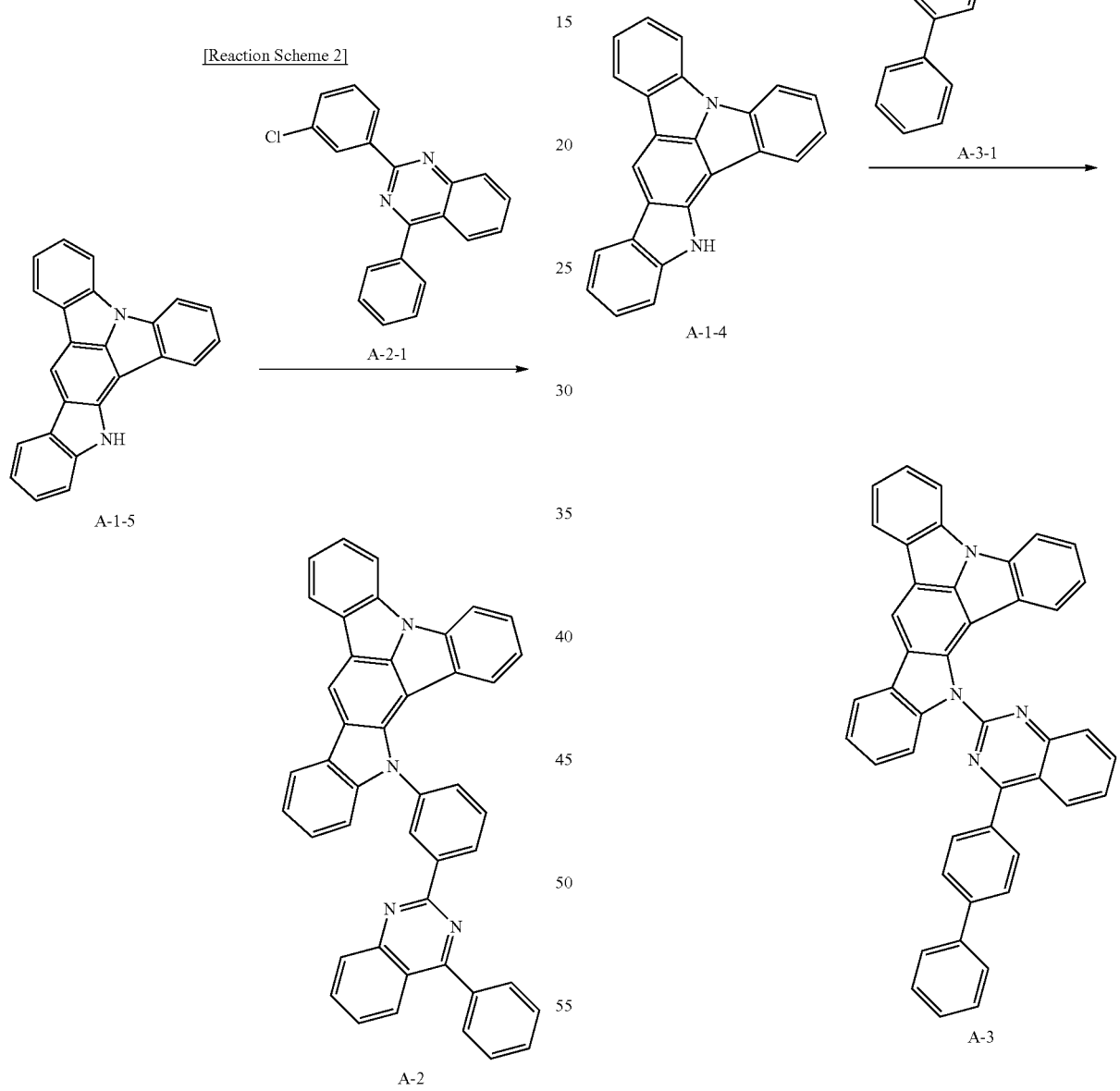

a) Synthesis of Compound A-2

Compound A-2 was synthesized according to the same method as d) of Synthesis Example 1 by using each one equivalent of Intermediate A-1-5 and Intermediate A-2-1 (2-chloro-4-phenyl-quinazoline, cas: 29874-83-7).

LC/MS calculated for: C44H26N4 Exact Mass: 610.2157 found for 611.22 [M+H].

a) Synthesis of Compound A-3

Compound A-3 was synthesized according to the same method as d) of Synthesis Example 1 by using each one equivalent of Intermediate A-1-5 and Intermediate A-3-1 (4-[1,1'-biphenyl]-4-yl-2-chloro-quinazoline, cas: 1262866-93-2).

LC/MS calculated for: C44H26N4 Exact Mass: 610.2157 found for 611.22 [M+H].

Synthesis Example 4: Compound A-12

Synthesis Example 5: Compound A-18

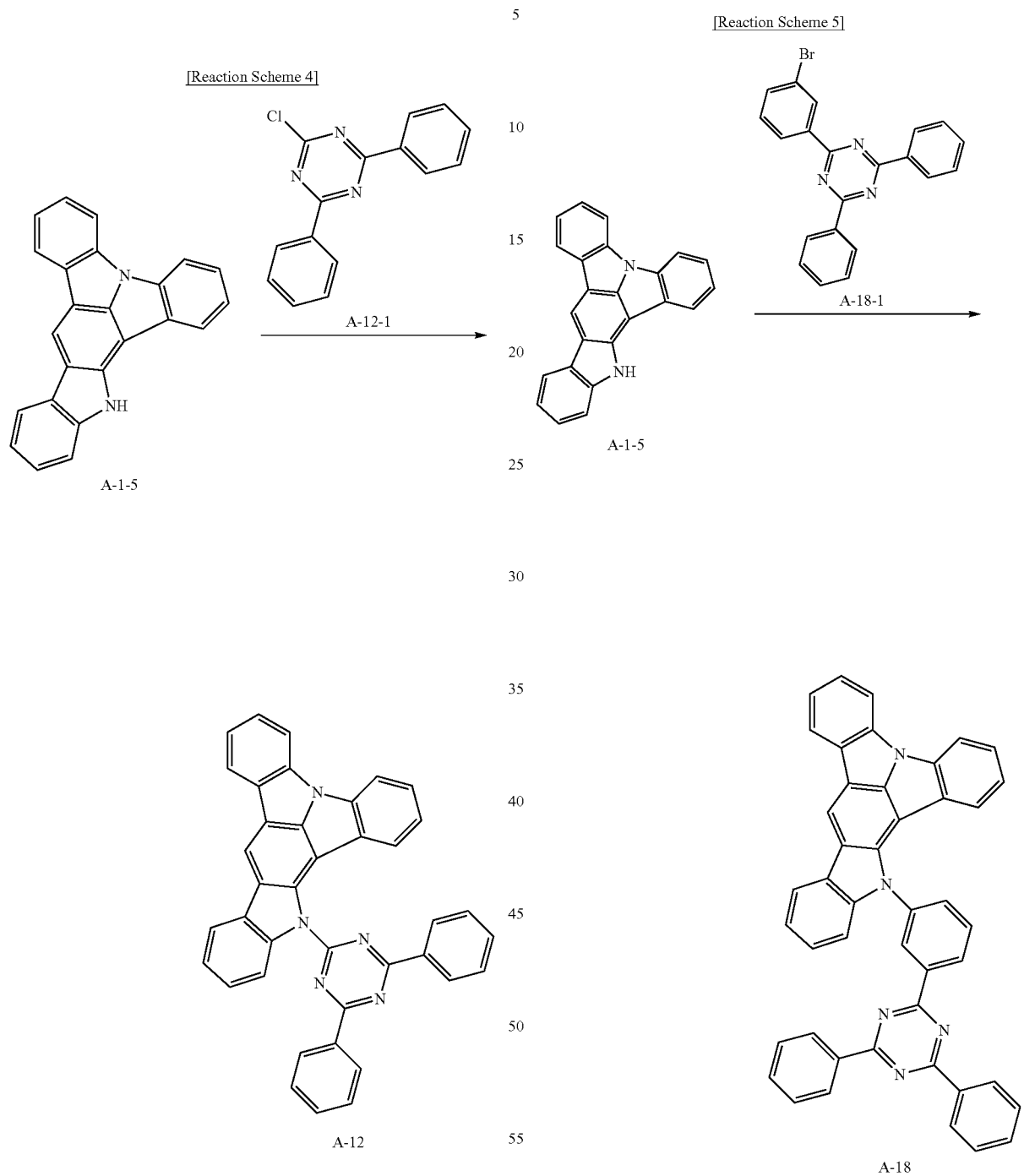

a) Synthesis of Compound A-12

Compound A-12 was synthesized according to the same method as d) of Synthesis Example 1 by using one equivalent of Intermediate A-1-5 and 1.2 equivalent of Intermediate A-12-1 (2-chloro-4,6-diphenyltriazine).

LC/MS calculated for: C39H23N5 Exact Mass: 561.1953 found for 562.20 [M+H].

a) Synthesis of Compound A-16

Compound A-18 was synthesized according to the same method as d) of Synthesis Example 1 by using 1 equivalent of Intermediate A-1-5 and 1.0 equivalent of Intermediate A-18-1 (2-(3-bromophenyl)-4,6-diphenyl-1,3,5-triazine, cas: 864377-31-1).

LC/MS calculated for: C45H27N5 Exact Mass: 637.2266 found for 638.23 [M+H].

Synthesis Example 6: Compound B-1

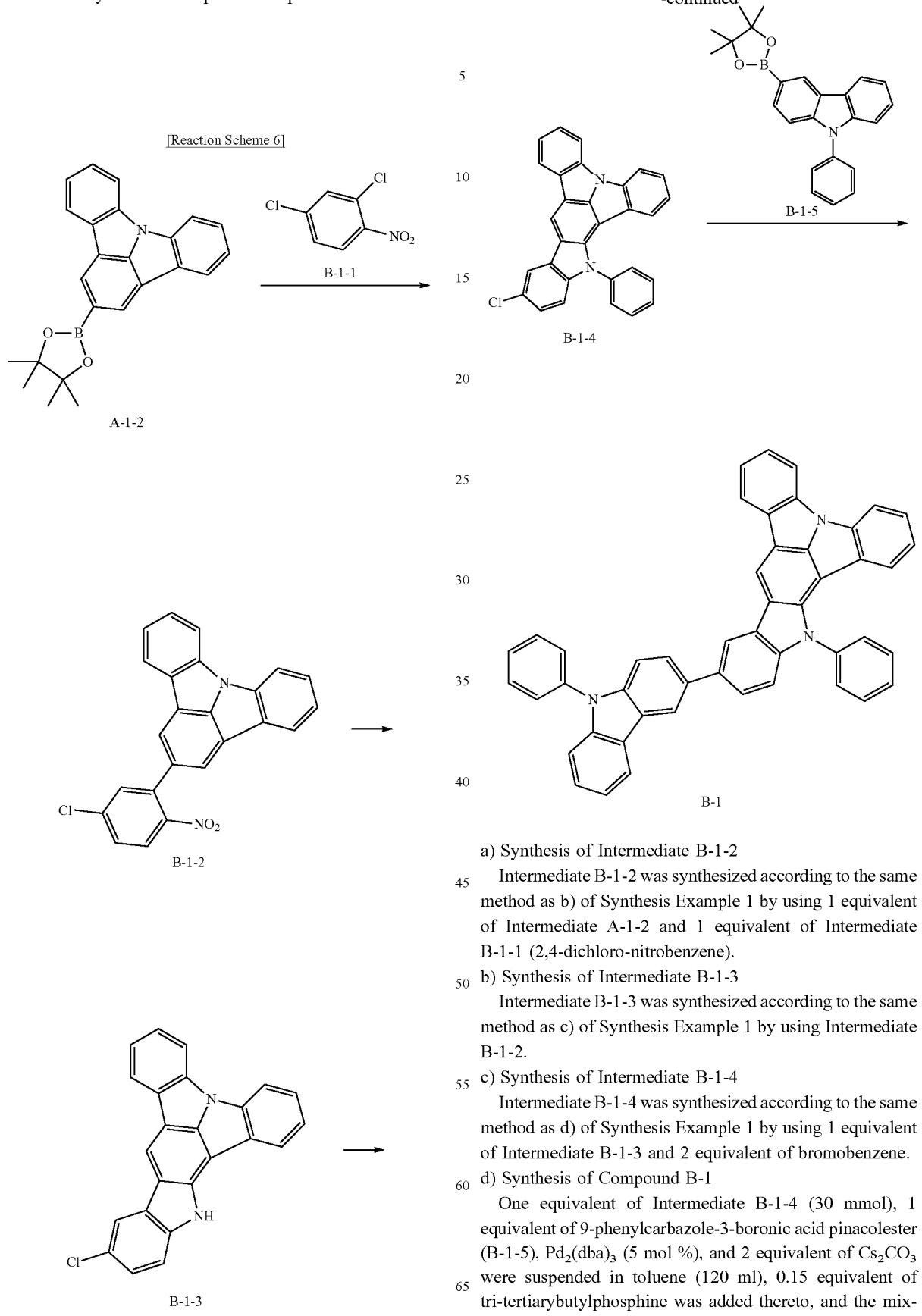

a) Synthesis of Intermediate B-1-2

Intermediate B-1-2 was synthesized according to the same method as b) of Synthesis Example 1 by using 1 equivalent of Intermediate A-1-2 and 1 equivalent of Intermediate B-1-1 (2,4-dichloro-nitrobenzene).

b) Synthesis of Intermediate B-1-3

Intermediate B-1-3 was synthesized according to the same method as c) of Synthesis Example 1 by using Intermediate B-1-2.

c) Synthesis of Intermediate B-1-4

Intermediate B-1-4 was synthesized according to the same method as d) of Synthesis Example 1 by using 1 equivalent of Intermediate B-1-3 and 2 equivalent of bromobenzene.

d) Synthesis of Compound B-1

One equivalent of Intermediate B-1-4 (30 mmol), 1 equivalent of 9-phenylcarbazole-3-boronic acid pinacolester (B-1-5), $Pd_2(dba)_3$ (5 mol %), and 2 equivalent of $Cs_2CO_3$ were suspended in toluene (120 ml), 0.15 equivalent of tri-tertiarybutylphosphine was added thereto, and the mixture was refluxed and stirred under a nitrogen current for 18 hours. When the reaction was complete, MeOH (300 mL) was added thereto, and the mixture was stirred. A solid precipitated therein was filtered and washed with water (300 mL). The solid was recrystallized with monochlorobenzene (200 mL) to obtain Compound B-1 (60% of a yield).

LC/MS calculated for: C48H29N3 Exact Mass: 647.2361 found for 648.24 [M+H].

Synthesis Example 7: Compound B-8

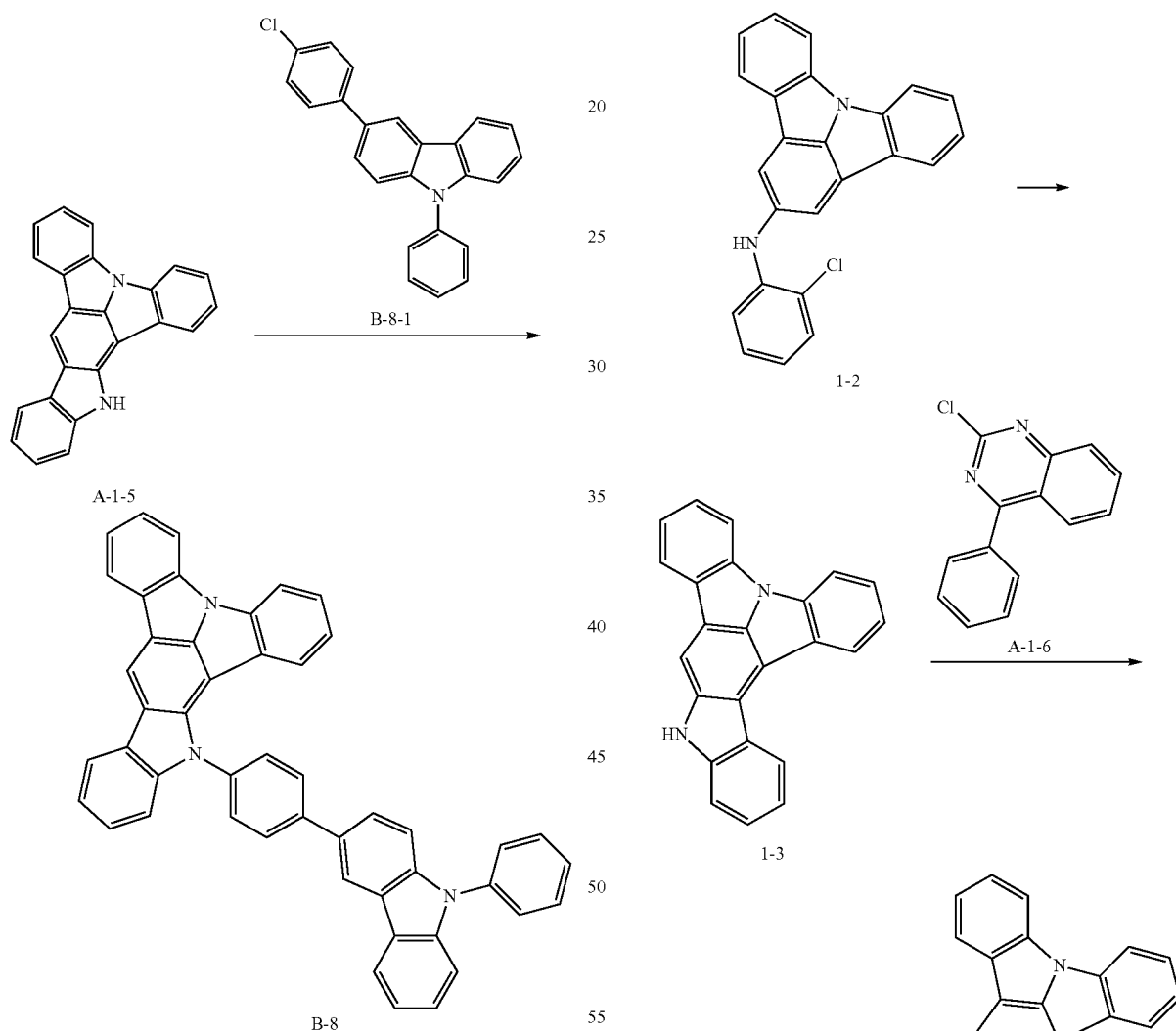

a) Synthesis of Compound B-8

Compound B-8 was synthesized according to the same method as d) of Synthesis Example 1 by using 1 equivalent of Intermediate A-1-5 and 1 equivalent of Intermediate B-8-1 (3-(4-chlorophenyl)-9-phenyl carbazole, refer to US 20150349270).

LC/MS calculated for: C48H29N3 Exact Mass: 647.2361 found for 648.24 [M+H].

Comparative Synthesis Example 1: Compound 1

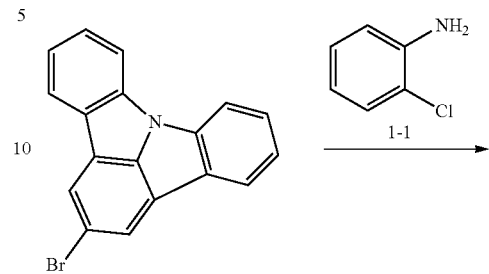

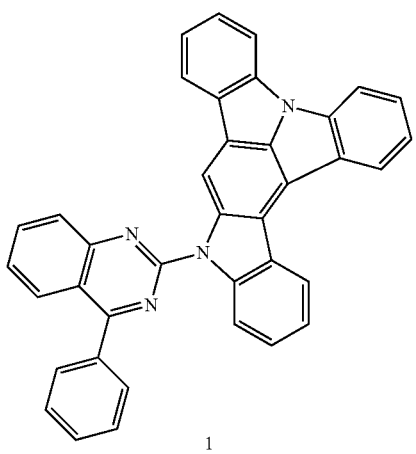

a) Synthesis of Intermediate 1-2

Intermediate 1-2 was synthesized according to the same method as d) of Synthesis Example 1 by using 1 equivalent of Intermediate A-1-1 and 1.2 equivalent of Intermediate 1-1 (2-chloroaniline). Then, a solid obtained therefrom was stirred under 1 M MeOH/Hex (1:1) and filtered to obtain Solid 1-2.

b) Synthesis of Intermediate 1-3

One equivalent of Intermediate 1-2 was dissolved to be 0.2 M in anhydrous acetamide in a 500 mL round-bottomed flask, 0.05 equivalent of palladium diacetate, 2 equivalent of cesium carbonate, and 0.15 equivalent of tricyclohexylphosphine tetrafluorate were added thereto, and the mixture was heated and refluxed under a nitrogen atmosphere. After 18 hours, a reaction solution was cooled down, and an organic layer therefrom was dried under a reduced pressure. Methanol was added thereto, and the mixture was stirred and filtered to obtain Intermediate 1-3 (70%=a yield).

c) Synthesis of Compound 1

Compound 1 was synthesized according to the same method as d) of Synthesis Example 1 by using 1 equivalent of Intermediate 1-3 and 1.2 equivalent of Intermediate A-1-6 (2-chloro-4-phenylquinazoline).

LC/MS calculated for: C38H22N4 Exact Mass: 534.1844 found for 535.19 [M+H].

Comparative Synthesis Example 2: Compound 2

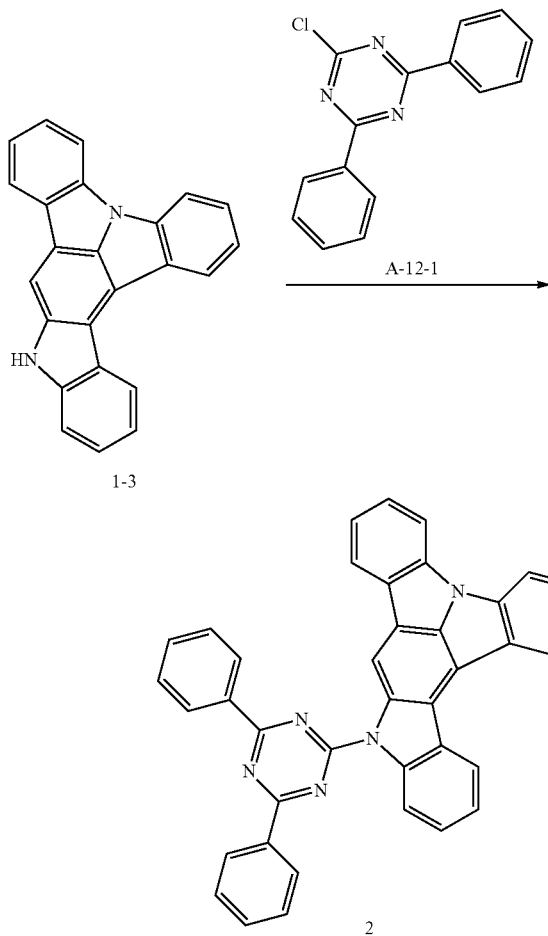

a) Synthesis of Compound 2

Compound 2 was synthesized according to the same method as d) of Synthesis Example 1 by using 1 equivalent of Intermediate 1-3 and 1.2 equivalent of Intermediate A-12-1 (2-chloro-4,6-diphenyltriazine).

LC/MS calculated for: C39H23N5 Exact Mass: 561.1953 found for 562.20 [M+H].

(Manufacture of Organic Light Emitting Diode)

Example 1

Manufacture of Red Device

A 1000 Å-thick ITO was used as an anode, and a 1000 Å-thick aluminum (Al) as a cathode. Specifically, the organic light emitting diode was manufactured in a method of ultrasonic wave-cleaning an ITO glass substrate in acetone, isopropyl alcohol, and pure water respectively for 15 minutes, and UV ozone-cleaning it for 30 minutes. On the substrate, HT-1 was vacuum-deposited to be 80 nm thick under a vacuum degree of $650 \times 10^{-7}$ Pa at a deposition rate of 0.1 to 0.3 nm/s. Subsequently, a 300 Å-thick light-emitting layer was formed using Compound A-1 under the same vacuum deposition condition and herein a phosphorescent dopant was simultaneously deposited. An amount of the phosphorescent dopant was 3 wt % based on a total amount 100 wt % of the light-emitting layer by controlling a deposition rate of the phosphorescent dopant. Bis(2-methyl-8-quinolinolate)-4-(phenylphenolato)aluminum (BAlq) was deposited on the light-emitting layer under the same vacuum deposition condition to form a 50 Å-thick hole blocking layer. Then, Alq3 was deposited under the same vacuum deposition condition to form a 200 Å-thick electron transport layer. LiF and Al were sequentially deposited on the electron transport layer as a cathode to manufacture an organic photoelectric device.

A structure of the red organic optoelectric device is ITO/HT-1 (80 nm)/EML (A-1 (97 wt %)+(piq)$_2$Ir(acac) (3 wt %), 30 nm)/Balq (5 nm)/Alq3 (20 nm)/LiF (1 nm)/Al (100 nm).

The HT-1 has the following structure.

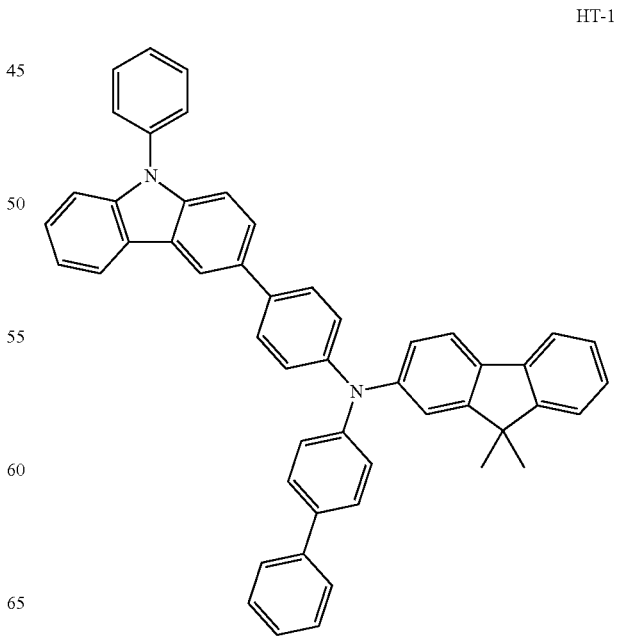

Example 2

An organic light emitting diode was manufactured according to the same method as Example 1 except for using Compound A-2 instead of Compound A-1.

Example 3

An organic light emitting diode was manufactured according to the same method as Example 1 except for using Compound A-3 instead of Compound A-1.

Example 4

An organic light emitting diode was manufactured according to the same method as Example 1 except for using a mixture of Compound A-1 and Compound B-1 in a weight ratio of 1:1 instead of Compound A-1 alone.

Example 5

An organic light emitting diode was manufactured according to the same method as Example 1 except for using a mixture of Compound A-1 and Compound B-8 in a weight ratio of 1:1 instead of Compound A-1 alone.

Comparative Example 1

An organic light emitting diode was manufactured according to the same method as Example 1 except for using CBP instead of Compound A-1.

Comparative Example 2

An organic light emitting diode was manufactured according to the same method as Example 1 except for using Compound 1 instead of Compound A-1.

Example 6

Manufacture of Green Device

A 1000 Å-thick ITO was used as an anode, and a 1000 Å-thick aluminum (Al) as a cathode. Specifically, the organic light emitting diode was manufactured in a method of ultrasonic wave-cleaning an ITO glass substrate in acetone, isopropyl alcohol, and pure water respectively for 15 minutes, and UV ozone-cleaning it for 30 minutes. On the substrate, HT-1 was vacuum-deposited to be 80 nm thick under a vacuum degree of $650 \times 10^{-7}$ Pa at a deposition rate of 0.1 to 0.3 nm/s. Subsequently, a 300 Å-thick light-emitting layer was formed using Compound A-12 under the same vacuum deposition condition and herein a phosphorescent dopant was simultaneously deposited. An amount of the phosphorescent dopant was 7 wt % based on a total amount 100 wt % of the light-emitting layer by controlling a deposition rate of the phosphorescent dopant. Bis(2-methyl-8-quinolinolate)-4-(phenylphenolato)aluminum (BAlq) was deposited on the light-emitting layer under the same vacuum deposition condition to form a 50 Å-thick hole blocking layer. Then, Alq3 was deposited under the same vacuum deposition condition to form a 200 Å-thick electron transport layer. LiF and Al were sequentially deposited on the electron transport layer as a cathode to manufacture an organic photoelectric device.

A structure of the green organic photoelectric device is ITO/HT-1 (80 nm)/EML (A-12 (93 wt %)+[Ir(ppy)$_3$] (7 wt %), 30 nm)/BAlq (5 nm)/Alq3 (20 nm)/LiF (1 nm)/Al (100 nm).

Example 7

An organic light emitting diode was manufactured according to the same method as Example 6 except for using Compound A-18 instead of Compound A-12.

Comparative Example 3

An organic light emitting diode was manufactured according to the same method as Example 6 except for using Compound 2 instead of Compound A-12.

Evaluation

A current density change, a luminance change, and luminous efficiency of each organic light emitting diode according to Examples 1 to 7 and Comparative Examples 1 to 3 were measured.

Specific measurement methods are as follows, and the results are shown in Table 1 and Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and, the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-span

Life-spans of the green organic light emitting diodes were measured as a time when their luminance decreased down to ½ relative to the initial luminance after emitting light with 12,000 nit as the initial luminance and measuring their luminance decrease depending on a time with a Polanonix life-span measurement system. Life-spans of the red organic light emitting diodes were measured as a time when their luminance decreased down to ½ relative to the initial luminance after emitting light with 50,000 nit as the initial luminance and measuring their luminance decrease depending on a time.

TABLE 1

| | | | | | | |
|---|---|---|---|---|---|---|
| | | | Red device | | | |
| | First host | Second host | First host + Second host ratio | Color | Efficiency Cd/A | Life-span (T90) |
| Example 1 | compound A-1 | — | — | red | 16 | 150 |

TABLE 1-continued

| | First host | Second host | First host + Second host ratio | Color | Efficiency Cd/A | Life-span (T90) |
|---|---|---|---|---|---|---|
| | | | Red device | | | |
| Example 2 | compound A-2 | — | — | red | 17 | 110 |
| Example 3 | compound A-3 | — | — | red | 15 | 130 |
| Example 4 | compound A-1 | compound B-1 | 5:5 | red | 18 | 190 |
| Example 5 | compound A-1 | compound B-8 | 5:5 | red | 17.5 | 220 |
| Comparative Example 1 | compound CBP | — | — | red | 5.8 | 20 |
| Comparative Example 2 | compound 1 | — | — | red | 13 | 70 |

Referring to the results of Table 1, Examples 1 to 3 showed improved characteristics in terms of luminous efficiency and a life-span compared with Comparative Examples 1 and 2. In addition, Examples 4 and 5 using a mixed host showed more improved characteristics in terms of luminous efficiency and a life-span when a HT material in a corresponding material group was used as a cohost.

TABLE 2

| | Host | Color | Efficiency Cd/A | Life-span (T90) |
|---|---|---|---|---|
| | | Green Device | | |
| Example 6 | Compound A-12 | green | 46 | 85 |
| Example 7 | Compound A-18 | green | 51 | 100 |
| Comparative Example 3 | Compound 2 | green | 42 | 40 |

Referring to the results of Table 2, Examples 6 and 7 showed improved characteristics in terms of luminous efficiency and a life-span compared with Comparative Example 3.

Based on these two above results, a triazine core as well as a quinazoline core according to Examples showed the same excellent characteristics compared with an isomer core according to Comparative Examples.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode
105: organic layer
110: cathode
120: anode
130: light-emitting layer

What is claimed is:
1. A compound for an organic optoelectric device represented by Chemical Formula 1:

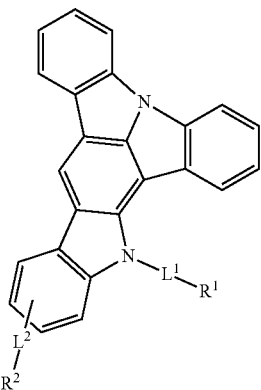

[Chemical Formula 1]

wherein, in Chemical Formula 1,
either:
a substituted or unsubstituted pyridyl group, a substituted or unsubstituted pyrimidinyl group, a substituted or unsubstituted triazinyl group, and $R^2$ is hydrogen, deuterium, a substituted or unsubstituted C6 to C30 aryl group, a substituted or unsubstituted carbazolyl group, a substituted or unsubstituted pyridyl group, a substituted or unsubstituted pyrimidinyl group, a substituted or unsubstituted triazinyl group, or a combination thereof, or (ii) $R^1$ is hydrogen, deuterium, a substituted or unsubstituted C6 to C30 aryl group, a substituted or unsubstituted pyridyl group, a substituted or unsubstituted pyrimidinyl group, a substituted or unsubstituted triazinyl group, or a combination thereof, and $R^2$ is a substituted or unsubstituted carbazolyl group, a substituted or unsubstituted pyridyl group, a substituted or unsubstituted pyrimidinyl group, a substituted or unsubstituted triazinyl group, $L^1$ and $L^2$ are independently a single bond or a substituted or unsubstituted C6 to C30 arylene group, and the "substituted" refers to replacement of at least one hydrogen by deuterium, a C1 to C30 alkyl group, a C6 to C30 aryl group, or a C2 to C30 monocyclic heteroaryl group, provided that the compound is not

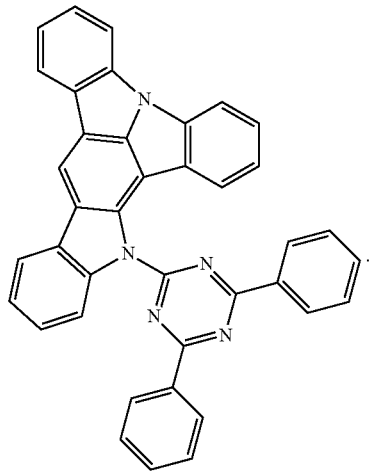 [SMILES: c1ccc(-c2nc(-c3ccccc3)nc(-n3c4ccccc4c4cc5c6ccccc6n6c7ccccc7c(c43)c56)n2)cc1]

2. The compound for an organic optoelectric device as claimed in claim 1, wherein the compound is represented by Chemical Formula 1-I, 1-II, or 1-III:

[Chemical Formula 1-I]

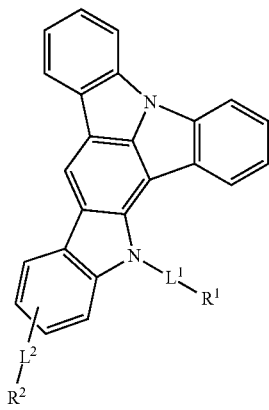

[Chemical Formula 1-II]

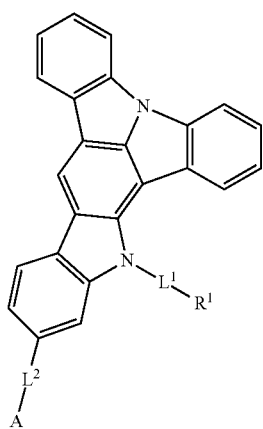

[Chemical Formula 1-III]

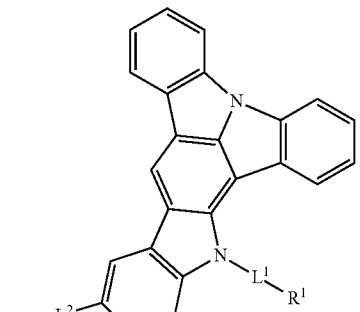

wherein, in Chemical Formula 1-I, $R^2$ is hydrogen, deuterium, a substituted or unsubstituted C6 to C30 aryl group, a substituted or unsubstituted carbazolyl group, a substituted or unsubstituted pyridyl group, a substituted or unsubstituted pyrimidinyl group, a substituted or unsubstituted triazinyl group, or a combination thereof, A is a substituted or unsubstituted pyridyl group, a substituted or unsubstituted pyrimidinyl group, a substituted or unsubstituted triazinyl group, and $L^1$ and $L^2$ are independently a single bond or a substituted or unsubstituted C6 to C30 arylene group, and wherein, in Chemical Formulae 1-II and 1-III, $R^1$ is hydrogen, deuterium, a substituted or unsubstituted C6 to C30 aryl group, a substituted or unsubstituted pyridyl group, a substituted or unsubstituted pyrimidinyl group, a substituted or unsubstituted triazinyl group, or a combination thereof, A is a substituted or unsubstituted carbazolyl group, a substituted or unsubstituted pyridyl group, a substituted or unsubstituted pyrimidinyl group, a substituted or unsubstituted triazinyl group, and $L^1$ and $L^2$ are independently a single bond or a substituted or unsubstituted C6 to C30 arylene group.

3. The compound for an organic optoelectric device as claimed in claim 2, wherein:

in Chemical Formula 1-I, A is a group of Group 1-A, and in Chemical Formulae 1-II and 1-III, A is a group of Groups 1-A and 1-B:

[Group 1-A]

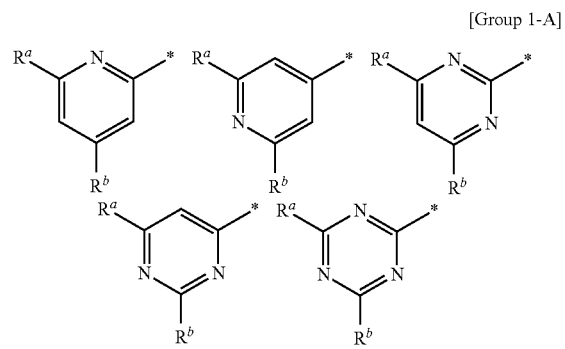

[Group 1-B]

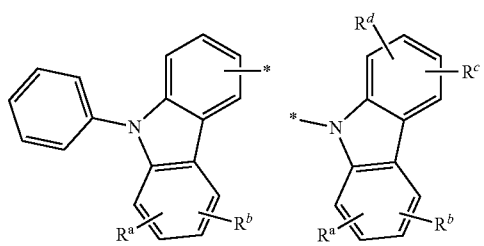

wherein, in Groups 1-A and 1-B, $R^a$ to $R^d$ are independently hydrogen, deuterium, C1 to C30 alkyl group, C6 to C30 aryl group, or C2 to C30 heteroaryl group, and

* indicates a binding site with an adjacent atom.

4. The compound for an organic optoelectric device as claimed in claim 3, wherein the substituents of Group 1-A are selected from substituents of Group 1-A1:

[Group 1-A1]

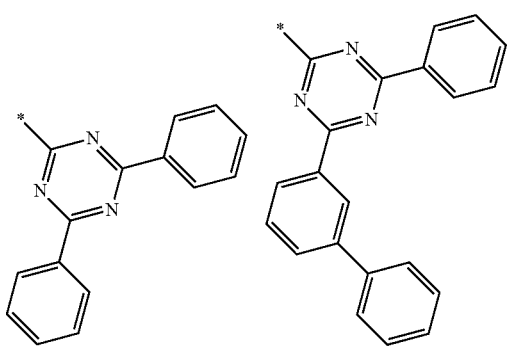

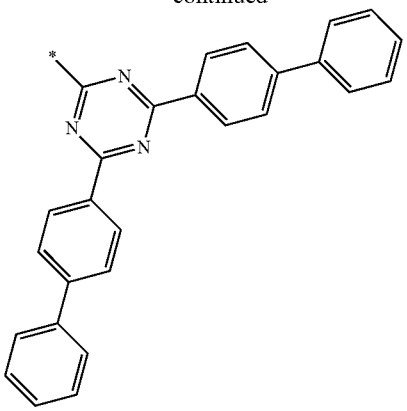

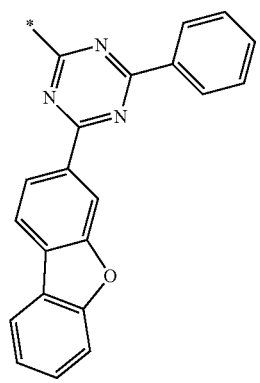

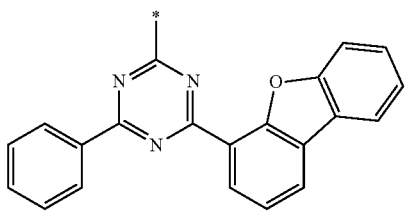

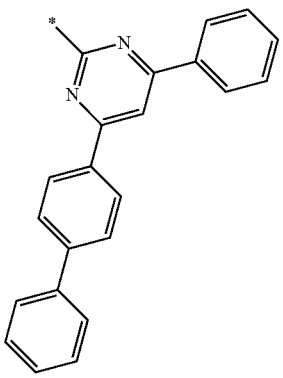

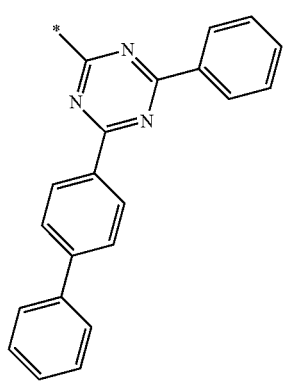

wherein, in Group 1-A1,

* indicates a binding site with an adjacent atom.

5. The compound for an organic optoelectric device as claimed in claim 3, wherein the substituents of Group 1-B are selected from substituents of Group 1-B1:

[Group 1-B1]

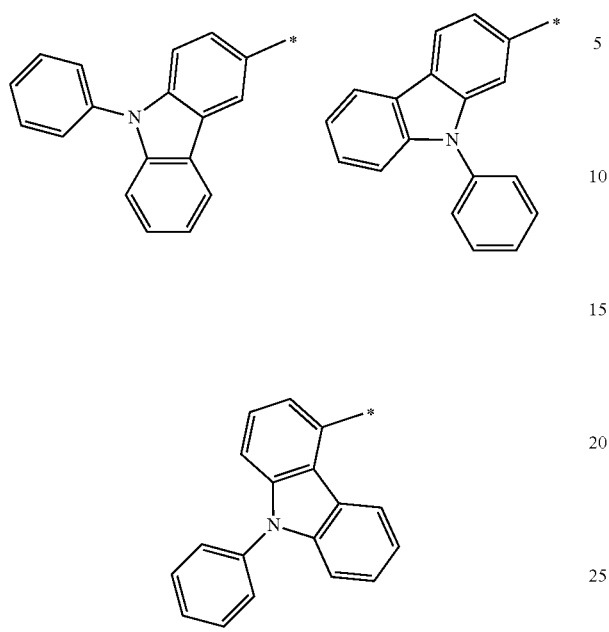

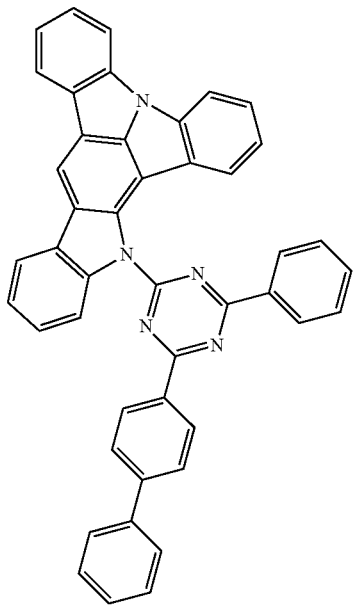
[A-14]

wherein, in Group 1-B1,

* indicates a binding site with an adjacent atom.

6. The compound for an organic optoelectric device as claimed in claim 1, wherein the $L^1$ and $L^2$ are independently a single bond, a substituted or unsubstituted phenylene group, a substituted or unsubstituted biphenylene group, or a substituted or unsubstituted terphenylene group.

7. The compound for an organic optoelectric device as claimed in claim 1, wherein the compound is selected from compounds of Group 2:

[Group 2]

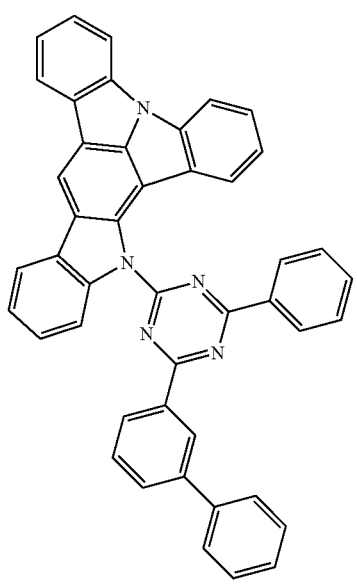
[A-13]

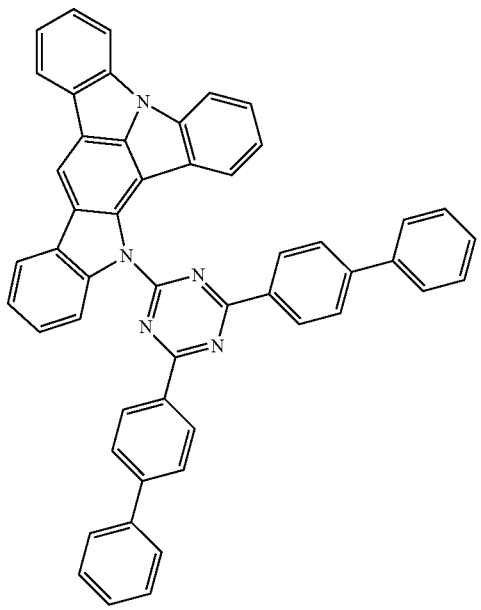
[A-15]

[A-16]
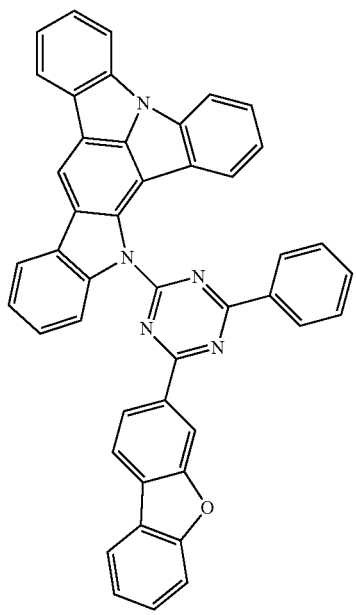
[A-17]
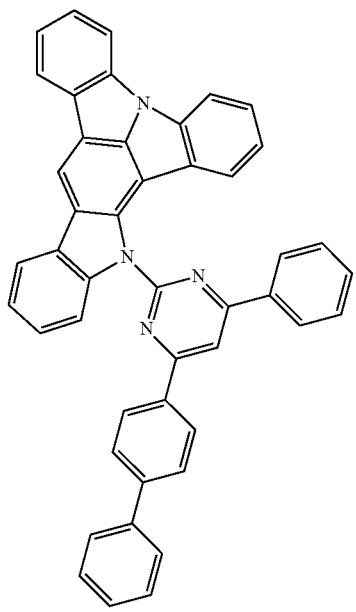
[A-18]
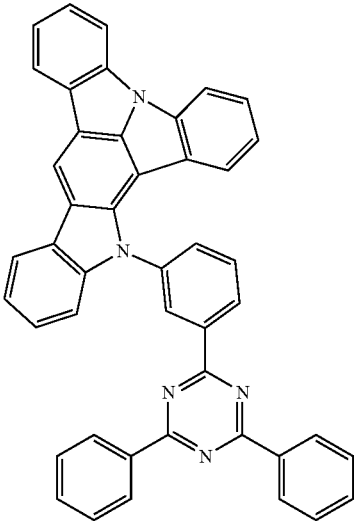
[A-19]
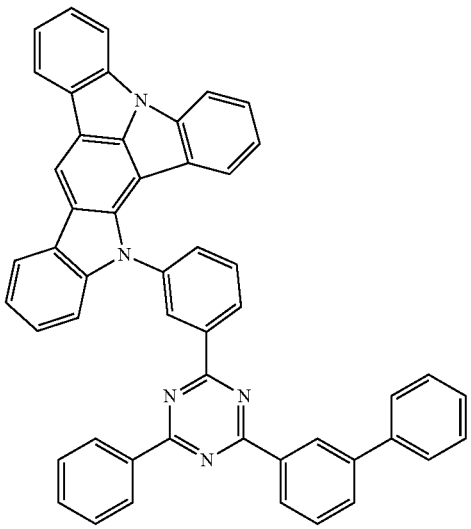

[A-20]
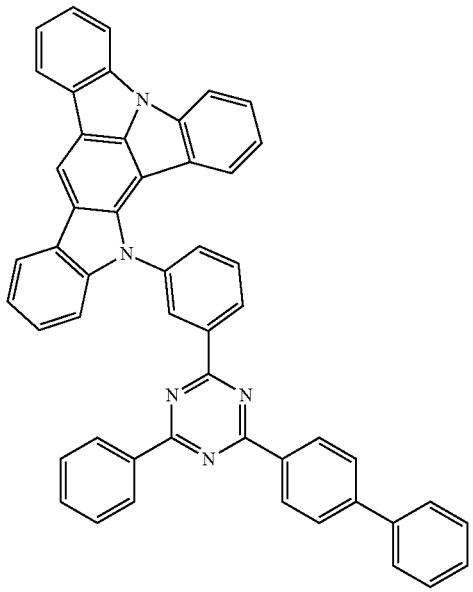
[A-21]
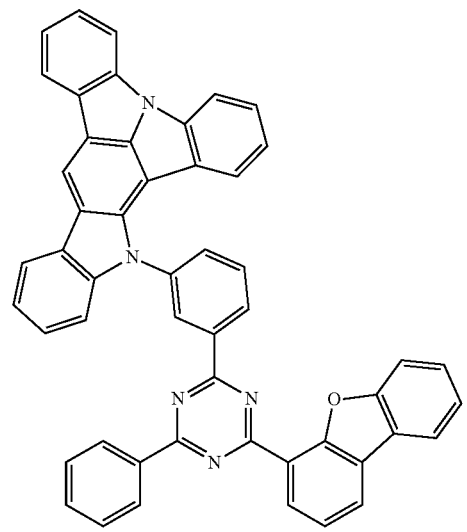
[B-1]
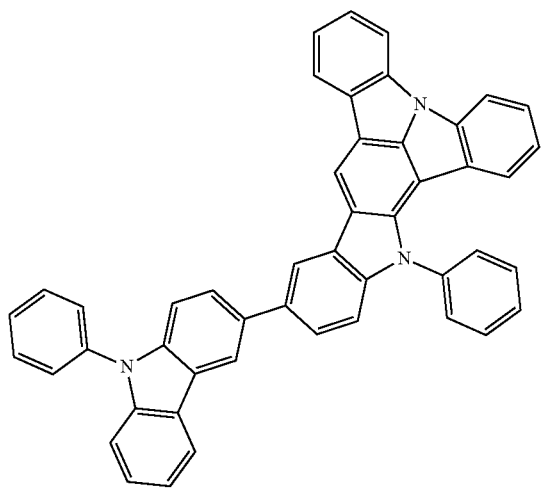
[B-2]
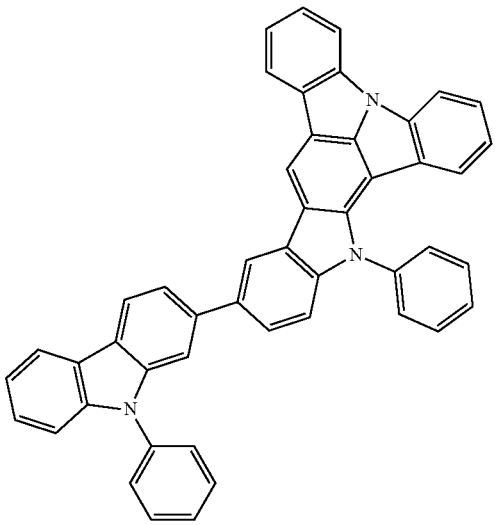
[B-3]
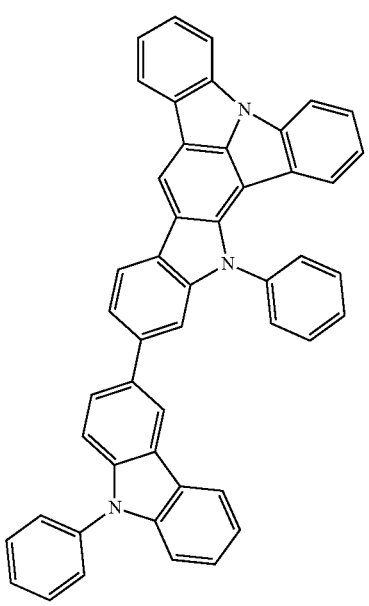
[B-4]
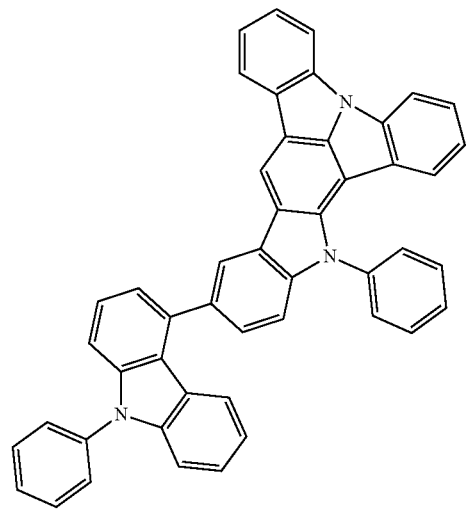

[B-5]
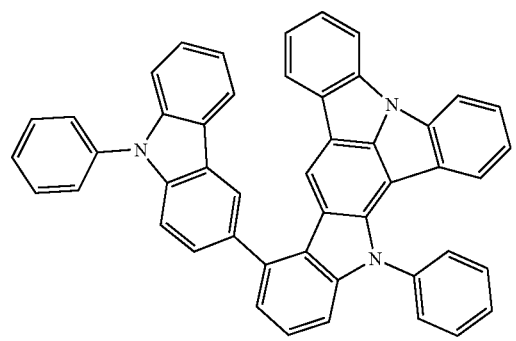
[B-6]
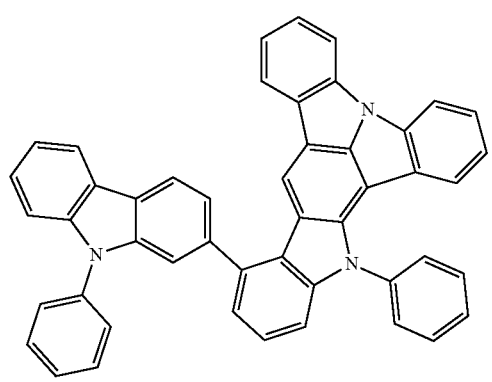
[C-5]
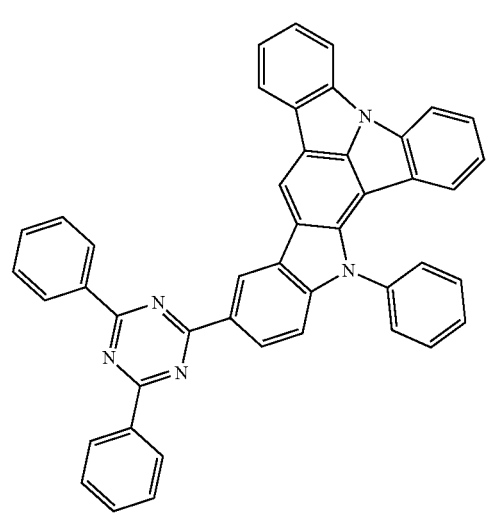
[C-6]
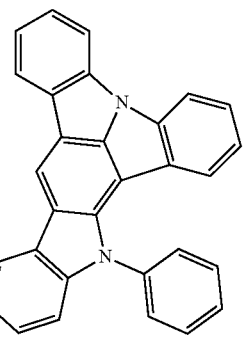
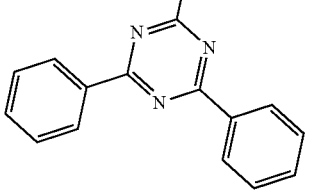
[C-7]
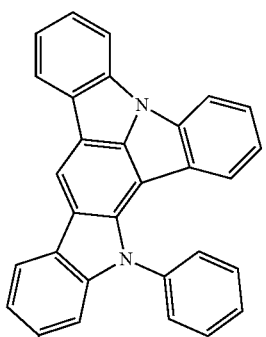
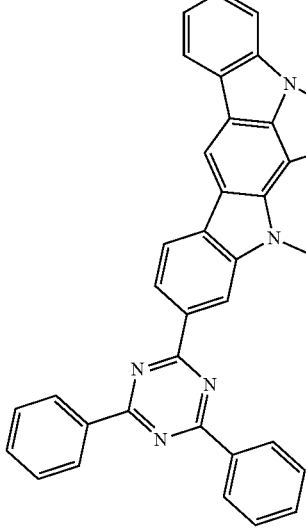
[C-8]
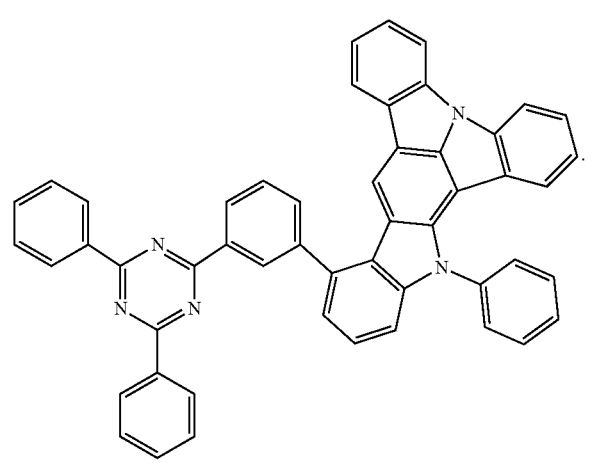

8. An organic optoelectric device comprising
an anode and a cathode facing each other, and
at least one organic layer disposed between the anode and the cathode,
wherein the organic layer includes the compound for an organic optoelectric device as claimed in claim 1.

9. The organic optoelectric device as claimed in claim 8, wherein the organic layer includes a light-emitting layer, and
the light-emitting layer includes the compound for an organic optoelectric device.

10. The organic optoelectric device as claimed in claim 9, wherein the compound for an organic optoelectric device is included as a host of the light-emitting layer.

11. A display device comprising the organic optoelectric device as claimed in claim 10.

12. A compound for an organic optoelectric device represented by Chemical Formula 1-II or Chemical Formula 1-III:

[Chemical Formula 1-II]

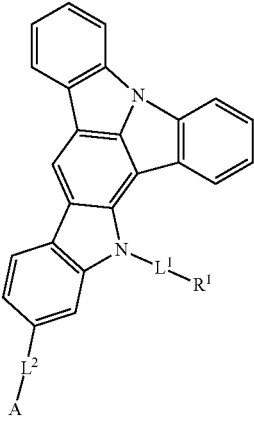

[Chemical Formula 1-III]

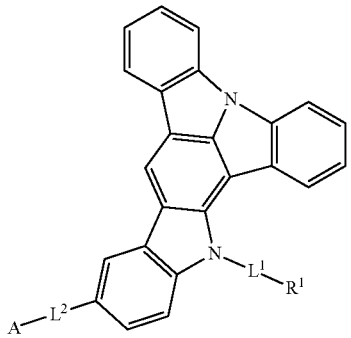

wherein, in Chemical Formulae 1-II and 1-III,
$R^1$ is hydrogen, deuterium, a substituted or unsubstituted C6 to C30 aryl group, a substituted or unsubstituted C2 to C30 monocyclic heterocyclic group, or a combination thereof,
A is an N-containing substituted or unsubstituted C2 to C30 heterocyclic group,
$L^1$ is a single bond, a substituted or unsubstituted C6 to C30 arylene group, or a substituted or unsubstituted C2 to C30 monocyclic heteroarylene group,
$L^2$ is a single bond, a substituted or unsubstituted C6 to C30 arylene group, or a substituted or unsubstituted C2 to C30 heteroarylene group,
in $L^1$ and $R^1$, the "substituted" refers to replacement of at least one hydrogen by deuterium, a C1 to C30 alkyl group, a C6 to C30 aryl group, or a C2 to C30 monocyclic heteroaryl group, and
in $L^2$ and A, the "substituted" refers to replacement of at least one hydrogen by deuterium, a C1 to C30 alkyl group, a C6 to C30 aryl group, or a C2 to C30 heteroaryl group.

13. The organic optoelectric device as claimed in claim 12, wherein:
the organic layer includes a light-emitting layer, and
the light-emitting layer includes the compound for an organic optoelectric device.

14. The organic optoelectric device as claimed in claim 13, wherein the compound for an organic optoelectric device is a host of the light-emitting layer.

15. A display device comprising the organic optoelectric device as claimed in claim 14.

* * * * *

UNITED STATES PATENT AND TRADEMARK OFFICE
CERTIFICATE OF CORRECTION

PATENT NO. : 11,056,655 B2
APPLICATION NO. : 15/473991
DATED : July 6, 2021
INVENTOR(S) : Kipo Jang et al.

Page 1 of 2

It is certified that error appears in the above-identified patent and that said Letters Patent is hereby corrected as shown below:

In the Claims

Claim 1 should read:
1. A compound for an organic optoelectric device represented by Chemical Formula 1:

[Chemical Formula 1]

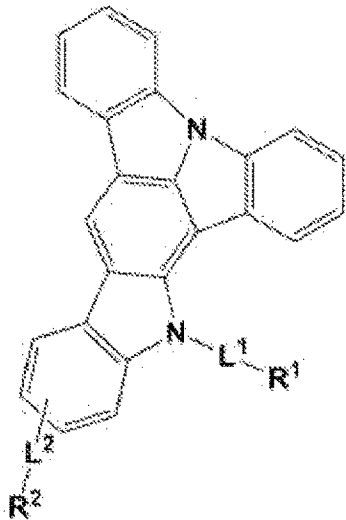

wherein, in Chemical Formula 1,
either:
 (i) $R^1$ is a substituted or unsubstituted pyridyl group, a substituted or unsubstituted pyrimidinyl group, a substituted or unsubstituted triazinyl group, and $R^2$ is hydrogen, deuterium, a substituted or unsubstituted C6 to C30 aryl group, a substituted or unsubstituted carbazolyl group, a substituted or unsubstituted pyridyl group, a substituted or unsubstituted pyrimidinyl group, a substituted or unsubstituted triazinyl group, or a combination thereof, or
 (ii) $R^1$ is hydrogen, deuterium, a substituted or unsubstituted C6 to C30 aryl Signed and Sealed this
Tenth Day of August, 2021

Drew Hirshfeld
*Performing the Functions and Duties of the
Under Secretary of Commerce for Intellectual Property and
Director of the United States Patent and Trademark Office* group, a substituted or unsubstituted pyridyl group, a substituted or unsubstituted pyrimidinyl group, a substituted or unsubstituted triazinyl group, or a combination thereof, and $R^2$ is a substituted or unsubstituted carbazolyl group, a substituted or unsubstituted pyridyl group, a substituted or unsubstituted pyrimidinyl group, a substituted or unsubstituted triazinyl group, $L^1$ and $L^2$ are independently a single bond or a substituted or unsubstituted C6 to C30 arylene group, and the "substituted" refers to replacement of at least one hydrogen by deuterium, a C1 to C30 alkyl group, a C6 to C30 aryl group, or a C2 to C30 monocyclic heteroaryl group, provided that the compound is not 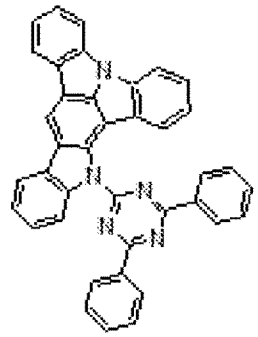 .